(12) United States Patent
Park et al.

(10) Patent No.: US 6,541,619 B1
(45) Date of Patent: Apr. 1, 2003

(54) FUSION PROTEIN OF HEGF AND HUMAN ANGIOGENIN AND PROCESS FOR PREPARING THE SAME

(75) Inventors: Myung-Hwan Park, Seoul (KR); Seung-Kook Park, Sungnam (KR); Jong-Myung Yoon, Sungnam (KR); Seung-Hee Han, Sungnam (KR); Byung-Kwon Oh, Sungnam (KR); Seung-Ho Kim, Seoul (KR); Young-Man Kim, Sungnam (KR); Tai-Young Koo, Suwon (KR); Byoung-Kwang Lee, Sungnam (KR)

(73) Assignee: Daewoong Pharmaceutical Co., Ltd., Kyunggi-do (KR)

( * ) Notice: Subject to any disclaimer, the term of this patent is extended or adjusted under 35 U.S.C. 154(b) by 0 days.

(21) Appl. No.: 09/530,685

(22) PCT Filed: Oct. 30, 1998

(86) PCT No.: PCT/KR98/00343
§ 371 (c)(1),
(2), (4) Date: Jul. 13, 2000

(87) PCT Pub. No.: WO99/23112
PCT Pub. Date: May 14, 1999

(30) Foreign Application Priority Data

Nov. 1, 1997 (KR) .............................. 97-57603

(51) Int. Cl.$^7$ ................. C12N 15/09; C12N 15/18; C12N 15/63; A61K 38/00
(52) U.S. Cl. ................... 536/23.4; 435/69.1; 435/69.4; 435/70.1; 435/325; 435/252.3; 435/320.1; 435/69.7; 514/2
(58) Field of Search ................ 435/69.1, 69.4, 435/69.7, 70.2, 325, 252.3, 320.1, 70.1; 514/2; 536/23.4

(56) References Cited

U.S. PATENT DOCUMENTS 5,840,840 A 11/1998 Rybak et al. ................ 530/350
5,916,794 A * 6/1999 Chandrasegaran .......... 435/199

FOREIGN PATENT DOCUMENTS

EP 0423641 A2 4/1991

OTHER PUBLICATIONS

*Biochemistry*, vol. 35, No. 2, 1996, pp. 545–553, Dianne L. Newton et al. "Angiogenin Single–Chain Immunofusions: Influence of Peptide Linkers and Spacers between Fusion Proteins".
*Biochemistry*, vol. 28, No. 4, 1989, pp. 1876–1884, J Wade Harper et al. "A Covalent Angiogenin/Ribanuclease Hybrid with a Fourth Disulfide Band Generated by Regional Mutagenesis".
John R. McDonald et al., Protein Expression and Purification 8:97–108, 1996.
Dianne L. Newton et al., Protein Engineering, 10(4):463–470, 1997.
Susanna M. Rybak et al., The Journal of Biological Chemistry, 266(31):21202–21207, 1991.
Susanna M. Rybak et al., Pro. Natl. Acad. Sci. USA, 89:3165–3169, 1992.
Monika Zewe et al., Immunotechnology, 3:127–136, 1997.
Jinno et al. Epidermal Growth Factor Receptor–Dependent Cytotoxicity For Human Squamous Carcinoma Cell Lines Of A Conjugate Composed of Human EGF and RNASE 1. Life Sciences 58/21 1901–1908 (1996).*
Yoon et al. Cloning And Cytotoxicity Of Fusion Proteins of EGF And Angiogenin. Life Science 64/16 1435–1445 (Mar. 12, 1999).*

* cited by examiner

Primary Examiner—Gary Kunz
Assistant Examiner—Regina M. DeBerry
(74) Attorney, Agent, or Firm—Darby & Darby

(57) ABSTRACT

The present invention provides a genetically engineered fusion protein consisting of hEGF that is internalized inside of the cells after tracing down the cancer cells expressing hEGF receptors and human angiogenin that is cytotoxic by degrading ribonucleotide upon internalization, a process for preparing a fusion protein in a large quantity by transforming *E. coli* with the expression vectors containing the gene encoding the fusion protein, and pharmaceutical application of the fusion protein as an anticancer agent. All components of the fusion protein form no antibodies and exhibit no immunotoxicity since they are derived from human. Each component alone is inactive to the cancer cells, however, once they are fused together, they kill the cancer cells selectively with a difference of 1000 fold in $IC_{50}$ in spite of its low molecular weight. Therefore, the fusion protein of the present invention is capable of treating the cancer expressing hEGF receptors at high level without showing toxicity.

12 Claims, 14 Drawing Sheets

FUSION PROTEIN OF HEGF AND HUMAN ANGIOGENIN AND PROCESS FOR PREPARING THE SAME

BACKGROUND OF THE INVENTION

1. Field of the Invention

The present invention relates to a fusion protein of human epidermal growth factor("hEGF") and human angiogenin, and a process for preparing the fusion protein, more specifically, to a fusion protein of hEGF that tracks down the cancer cells expressing hEGF receptors at high level following internalization and angiogenin that exhibits cytotoxicity by degrading ribonucleic acids upon internalization, a process for preparing the fusion protein which employs *E. coli* transformed with an expression vector encoding a gene for the fusion protein, and its therapeutic application as an anticanacer agent.

2. Description of the Prior Art

Environmental pollution and increase in population of old-aged people cause increase of the rate of cancer by 5% every year. Cancer ranks first as the major cause of death among other diseases and accidents.

Chemotherapy has been widely used as an effective way to prevent and cure cancer. However, it has been known that chemotherapy provokes various side-effects, e.g., attacking the normal cells as well as the cancer cells. Due to low specificity for the cancer cells and toxicity for the normal cells, numerous attempts have been made to develop anti-cancer agents with high specificity and low toxicity. The examples of such attempts include search for the drug with novel mode of action, development of drug delivery system and drug targeting, and use of a secondary agent to aid activity of a primary anticancer agent.

Recently, a new method of drug targeting has been studied that is selectively active to the cancer cells by using a chemical agent bound to a carrier which has strong affinity to the cancer cells. As a promising resolution, it has been reported that antibodies against to antigens specific to the cancer cells, such as alpha-fetoprotein, are bound to the chemical agents, ricin, Diphtheria toxin, Pseudomonas toxin, or radioisotopes(see: K. Shikoro et al., Br. Med. Bull., 40:233–239(1984); Vijay et al., Nature, 339:394–397(1989); U.S. Pat. No. 4,545,985; Peter et al., Cancer Res., 54:1008 (1994)). However, the antibody-bound chemical agents have some shortcomings, such as difficulty in penetrating the cells, antigenicity of antibody itself, binding to the normal cells, low binding efficiency due to relatively high molecular weight of antibody(see: Pastan et al., Cell, 47:641–648 (1986); Hurwitz et al., Cancer Res., 35:1175–1181(1975); Delabye et al., J. Clin. Invest., 77:301–311(1986); Buchegger et al., J. Exp. Med., 158:413–427(1986); Buchegger et al., Cancer, 58:655–661(1986)).

Another attempt has been made to develop an anticancer agent using polyamino acids as a carrier since polyamino acids do not exhibit toxicity to the normal cells. After the agent forms a complex by binding to the polyamino acids, it is detached from the complex by the enzymes present in the cancer cells. However, this strategy failed to solve the aforementioned problems(see: Kato et al., J. Med. Chem., 27:1602–1607(1984); EP 112,720; U.S. Pat. No. 4,485,093).

As one of attempts for anticancer drug targeting, formation of a protein complex between a toxic protein and a peptide or, a protein capable of binding to the intracellular receptors has been extensively studied, though it has not been fruitful. Such peptides or proteins are TGF(tumor growth factor), MSH(melanocyte stimulating hormone), somatostatin, glucagon, insulin, transferrin, LDL(low density lipoprotein), calcitonin, alpha-2-macroglobulin, bradykinin, and EGF(see: U.S. Pat. No. 4,545,985; Shimizu et al., FEBS Letters, 118:274–278(1980); Cawley et al., Cell, 22:563–570(1980); Simpson et al., Cell, 29:469–473 (1982); WO85/00369; WO83/04030; U.S. Pat. No 4,528,186; EP 46,039; EP 128,733; WO85/01284; EP 131,868; U.S. Pat. No. 3,917,824).

Also, genetically engineered fusion proteins of peptides and cytotoxins have been generated by binding Diphtheria toxin to TRH(thyrotropin releasing hormone), TRF (transferrin), MSH, and LDL. Usage of these fusion proteins, however, has been restricted due to difficulties in maintaining the receptor binding activity of carrier proteins (see: Bacha et al., J. Biol. Chem., 258:1565–1570(1983); Okeefe et al., J. Biol. Chem., 260:932–937(1985); Murphy et al., Proc. Natl. Acad. Sci., USA, 83:8258–8262 (1986); Japanese Patent Publication No.(Sho)60-163824).

Toxicity of a protein complex of EGF and a cytotoxic chemical has not been lowered due to toxicity of the cytotoxic chemical itself and immunotoxicity resulted from antibody formation against the chemical(see: WO88/00837). EP 467,536 describes that genetically engineered TGF-fused to modified Pseudomonas exotoxin A can be used to target bladder cancer. However, it failed to overcome antigenicity of the toxin derived from the microorganism. Japanese Patent Publication No.(Sho) 63-41418 discloses a protein conjugate of EGF and Pseudomonas toxin using a chemical material as a linker. Again, toxicity issue raised by Pseudomonas toxin has remained to be solved. EP 11111 suggests an anticancer agent which is prepared by chemical conjugation of a low molecular weight growth factor with a chemical which binds non-specifically to carboxyl terminal or β-amino terminal of the protein. The prior art is, however, proven to be less satisfactory in the senses of contamination during chemical reaction, denaturation of the protein, and heterogeneicity of the conjugate itself.

As mentioned above, research on the cytotoxic agents or microorganism-derived toxins fused to monoclonal antibodies recognizing molecules on the surface of the cancer cells(see: U.S. Pat. No. 4,664, 911; U.S. Pat. No. 4,545,985) or studies on the fusion proteins generated by fusing a growth factor originated from neoplastic tissue and a microorganism-derived toxin(see: Jill et al., J. Biol. Chem., 266:21118(1991); Daniel et al., Cell, 22:563–570(1980); Caudhary et al., Proc. Natl. Acad. Sci., USA, 84:4538–4542 (1987)) are still ongoing, however, they have not been fruitful since these studies still need to overcome the problems caused by toxicity of the proteins, chemical contamination, immunotoxicity resulted from antibody formation, non-specific binding of antibodies, difficulty in delivering a high molecular weight fusion protein to the target cells(see: Chung et al., Mol. Cells, 6:125–132(1996)).

SUMMARY OF THE INVENTION

The present inventors have made an effort to solve the aforementioned problems of the immunotoxicity resulted from antibody formation and the low targeting efficiency due to a high molecular weight of at least 50 kD, and finally developed a genetically engineered low molecular weight fusion protein consisting of hEGF and angiogenin both of which normally exist in human body and then exhibit no toxicity following overdose administration. Further, the inventors manufactured a large quantity of the fusion protein by cloning and expressing a fusion gene encoding hEGF and angiogenin in bacteria, whose efficacy is substantially improved in comparison with the conventional anticancer agents in the senses that: 1) it selectively inhibits the growth of the cancer cells expressing hEGF receptor; 2) it does not have a detrimental effect on the growth of the normal cells; 3) it does not exhibit toxicity of the conventional chemical anticancer agents; and, 4) it does not cause any serious problem by forming antibody against the fusion protein.

A primary object of the present invention is, therefore, to provide a fusion protein of hEGF and angiogenin that selectively inhibits growth of the cancer cells expressing hEGF receptors.

The other object is to provide a process for preparing the fusion protein by employing recombinant microorganism transformed with an expression vector containing the gene encoding the fusion protein.

Another object is to provide an anticancer agent comprising the fusion protein as an active ingredient.

BRIEF DESCRIPTION OF DRAWINGS

The above and the other objects and features of the present invention will become apparent from the following description given in conjunction with the accompanying drawings, in which.

DETAILED DESCRIPTION OF THE INVENTION

Figure 1:
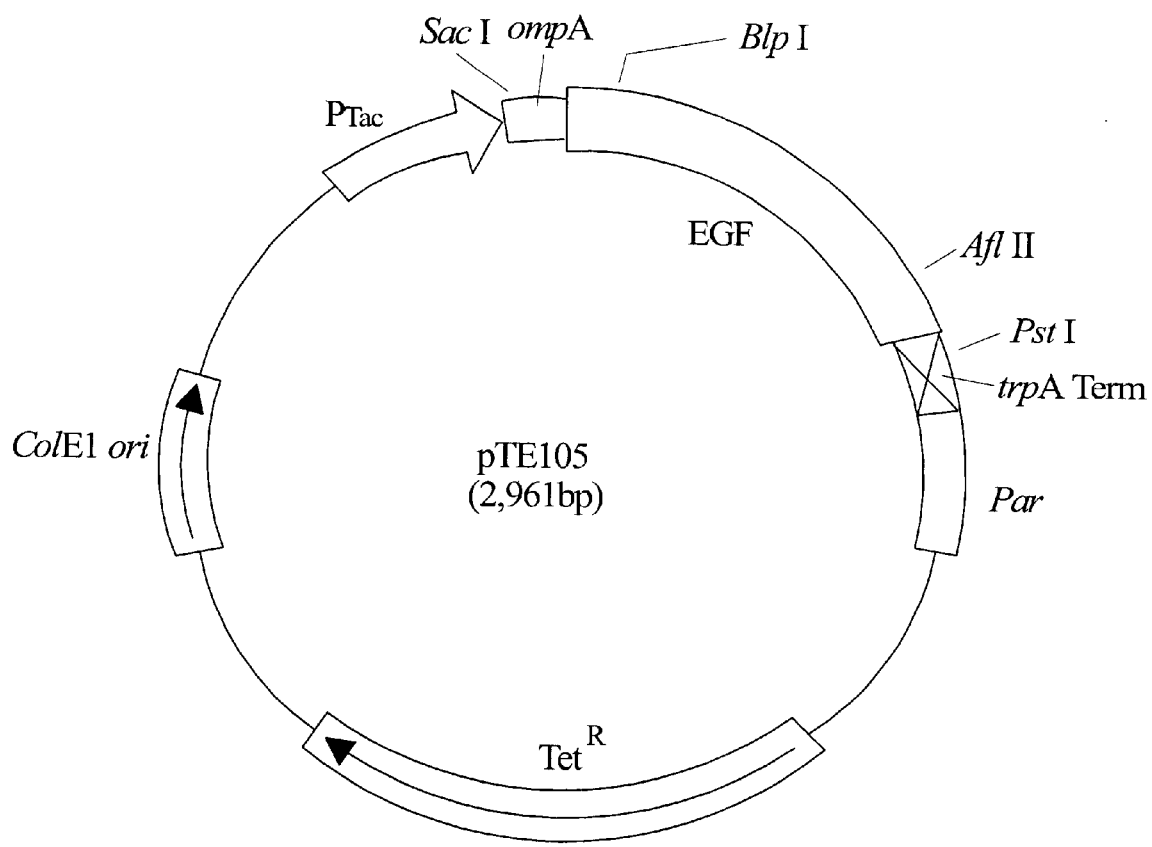
FIG. 1 is a plasmid map of an expression vector pTE105.

A fusion protein newly developed in the present invention is formed by connecting a tracer protein of hEGF and a toxic protein of angiogenin that belongs to ribonuclease superfamily through the aid of a appropriate linker, in order to allow proper folding of each protein molecule. As a result, the fusion protein consists of three components: a tracer of hEGF that tracks down the cancer cells; a cytotoxin of angiogenin that kills them; and, a linker which connects the hEGF and the angiogenin to ensure their biological activities. In this regard, hEGF functions to target the fusion protein to the cancer cells expressing hEGF receptors and then becomes internalized in the form of a fusion protein; angiogenin functions to kill the cancer cells by degrading ribonucleic acids upon internalization through a tracer; and, the linker peptide connects the tracer(i.e., hEGF) to the cytotoxin(i.e., angiogenin) and maintains their tertiary structure.

As described aboves, the present invention provides a novel fusion protein that successfully overcomes problems of the conventional anticancer agents, such as low targeting efficiency, chemical contamination during manufacturing, antigenicity of a fusion protein, toxicity of a cytotoxin.

In the past, fusion proteins used as anticancer agents have exhibited toxicity resulted from antibody formation within 1 week post-administration because of antigenicity induced by the antibody used as a tracer or toxicity of a cytotoxin derived from microorganism. Especially, in the case of fusion protein made of Diphtheria toxin or Pseudomonas toxin, the fusion proteins were not effective for the cancer cells any more, since most of the patients had already had antibodies to the fusion proteins prior to drug administration.

On the other hand, a tracer and a cytotoxin employed in the fusion protein of the invention always exist in human body so that the cytotoxin exhibits cytotoxicity only when it is delivered to the target cells by the tracer and then is internalized inside of the cells, which, in turn, provides no toxicity outside of the cells.

In general, to increase targeting efficiency of a fusion protein to the cancer cells, it is more favourable to use a fusion protein of small size. In the present invention, targeting efficiency has been much improved by using small molecular weight proteins, which are 6 kD hEGF and 14.4 kD angiogenin. Considering that the conventional fusion proteins are at least 50 kD, a 20.4 kD (6 kD+14.4 kD) fusion protein of the invention is strikingly small in its molecular weight.

In addition, to solve the problems of protein denaturation and contamination during chemical conjugation, the inventors did not employ a chemical process, instead, they introduced genetic engineering technique that the genes for a tracer and a cytotoxin are fused through a appropriate linker and then a fusion protein is produced in recombinant microorganism transformed therewith. In this process, each protein component is linked in the molecular ratio of 1:1 or 1:0.5–2 (tracer:toxic protein). As a linker, it is preferable to use a peptide consisting of the appropriate number of amino acids to maintain activity of each protein component, such as, a peptide composed of 0 to 20 amino acids, though glycine, (glycine)$_4$ serine, or [(glycine)$_4$ serine]$_2$, is most preferred.

As a tracer protein, it is possible to use not only human EGF but also animal EGF, TGF, their derivatives, and any low molecular weight peptide or protein which is capable of binding to hEGF receptors. As a cytotoxin, it is possible to use not only angiogenin degrading intracellular RNA but also any human ribonuclease, EDN(eosinophil derived neurotoxin), and their derivatives which belong to ribonuclease superfamily. A cytotoxin can bind to N-terminal or C-terminal of a tracer molecule, though it is more preferable to link N-terminal of a cytotoxin to C-terminal of a tracer.

Features of hEGF employed as a tracer in the fusion protein of the invention are as following:

1. It is selectively active only on the cancer cells that express hEGF receptors at high level and is not active on the normal cells.

2. It is applicable to a broad spectrum of cancers as long as hEGF receptors are expressed at high level in he cancer cells.

3. It delivers a cytotoxin efficiently since it is internalized inside of the cancer cells in the form of a fusion protein.

4. It is a 6 kD protein consisting of 53 amino acids which is small enough to penetrate the cells with ease.

5. It fuses with a cytotoxin with ease since it does not go through the post-translational modification.

Features of angiogenin which is employed as a cytotoxin in the fusion protein of the invention are as following:

1. It does not induce antibody formation since it is originated from human(present at 0.4 $\mu$g/ml in human blood).

2. It has tRNase activity in the cell and exhibits toxicity only inside of the cell upon internalization.

3. It has small size(14.4 kD protein consisting of 123 amino acids) in comparison with other microorganism-derived toxins such as Diphtheria toxin and Pseudomonas toxin, or plant-derived toxin such as ricin so that it is delivered to the target with ease.

The use of the fusion protein with the aforementioned features is broad as an anticancer agent for the cancers that express hEGF receptors, such as bladder cancer, lung cancer, brain cancer, breast cancer, skin cancer, and prostate cancer.

As a method for administration of the medicaments containing a fusion protein of the invention as an active ingredient, parenteral administration(e.g., rectal administration, subcutaneous injection, i.v. injection) is preferable, though oral administration may be used as well. Medicaments can be prepared in the form of tablets, capsules, pills, granules, fine subtilae, sublingual tablet, dragees, ointment, suppository, syrup, and suspension. Medicaments contain pharmaceutically acceptable carriers, such as diluents, disintegrators, bases, isotonic agents, binders, buffers, coating agents, adsorbents, lubricants, solvents, stabilizing agents, antioxidants, preservatives, sweetening agents, emulsifying agents, coloring agents, etc.

More specifically, pharmaceutically acceptable carriers are as following:

For diluents, there are starch and starch derivatives (e.g., dextrin, carboxymethyl starch), cellulose and cellulose derivatives(e.g., methyl cellulose, hydroxypropyl methyl cellulose), sugar(e.g., galactose, fructose, glucose), silicic acid and silicate(e.g., naturally occurring aluminium silicate, magnesium silicate), carbonates(calcium carbonate, magnesium carbonate, sodium hydrogencarbonate), synthetic hydrotalcite, polyoxyethylene derivatives, aluminium magnesium hydroxide, glycerine monostearate, sorbitan monooleic acid, etc.

For binders, there are starch and starch derivatives(e.g., $\alpha$-starch, dextrin), cellulose and cellulose derivatives (ethylcellulose, sodium carboxymethylcellulose, hydroxypropylmethyl cellulose), gum Arabic, gelatin, sugar(e.g., glucose, fructose), ethanol, gum tragacanth, polyvinyl alcohol, etc.

For disintegrators, there are starch and starch derivatives (carboxymethyl starch, hydroxypropyl starch), cellulose and cellulose derivatives(sodium carboxymethyl cellulose, cellulose crystal, hydroxypropylmethyl cellulose), carbonates (calcium carbonate, calcium hydrogencarbonate), gelatin, gum tragacanth, sugar, etc.

For lubricants, stearic acid, calcium stearate, magnesium stearate, talc, silicic acid and silicate(e.g., hard silicic anhydride, naturally occurring aluminium silicate), titanic oxide, calcium hydrogenphosphate, dried aluminium hydroxide gel, macrogol, etc.

For preservatives, there are p-hydroxybenzoate, sulfites (e.g., sodium pyrosulfites, sodium sulfite), phosphates (e.g., sodium phosphate, calcium polyphosphate, sodium poly phosphate, sodium methaphosphate), alcohol (e.g., chlorobutanol, benzyl alcohol), benzalkonium chloride, benzethonium chloride, phenol, cresol, chlorocresol, dihydroacetic acid, sodium dihydroacetic acid, glycerin, sorbic acid, sugar, etc.

For antioxidants, sulfites(e.g., sodium sulfite, sodium hydrogensulfite), rongalite, erythorbic acid, L-ascorbic acid, cysteine, thioglycerol, butylhydroxyanisol, propylgallic acid, ascorbyl palmitate, dibuthylhydroxy toluen, dl-$\alpha$-tocoperol.

For isotonic agents, glucose, glycerine, dextrin, sodium chloride, sodium nitrite, potassium nitrite, etc.

For buffers, sodium carbonate, hydrogen chloride, phosphates, boric acid, etc.

For coating agents, there are cellulose derivatives (e.g., hydroxypropyl cellulose, cellulose acetate phthalate, hydroxypropyl methylcellulose phthalate), shellac, poly vinylpyrrolidone, polyvinylpyridine(e.g., poly-2-vinylpyridine, poly-2-vinyl-5-ethylpyridine), polyvinylacetyl diethyl amino acetate, polyvinylalcohol phthalate, methacrylate, methacrylate co-polymer, etc.

For sweetening agents, there are sugar(glucose, fructose, lactose), sodium saccharine, sugar alcohol, etc.

For solvents, there are ethylendiamine, nicotin amide, sodium saccharine, citric acid, sodium citrate, sodium benzoate, polyvinylpyrrolidone, polysolvate, sorbitan fatty acid ester, glycerine, propylene glycol, benzyl alcohol, etc.

For bases, there are fat(lard), plant oil(e.g., olive oil, sesame seed oil), animal oil, lanolin acid, petrolatum, paraffin, wax, resin, bentonite, glycerine, glycol oil, fatty alcohol(e.g., stearylalcohol, cetanol), etc.

For dispersing agents, gum Arabic, gum tragacanth, cellulose derivatives(methylcellulose), stearic polyester, sorbitan sesquioleate, aluminium monostearic acid, sodium alginate, polysolbate, sorbitan fatty acidic ester, etc.

For stabilizing agents, there are sulfites(sodium sulfite), nitrogen, carbon dioxide, etc.

Medicaments contain a fusion protein of the invention at a concentration of 0.01 to 100%(w/w), though the amount varies according to the dosage form of the medicaments.

Administration dose depends on the body weight of the patients, seriousness of the disease, and doctor's opinion. However, it is generally advisable to administer 0.01 to 10 mg/kg body weight a day, preferably 0.02 to 2 mg in case of injection. Other than injection, it is advisable to take it into consideration the concentration of the fusion protein circulating in the blood.

Daily dose can be administered once or several times according to seriousness of the disease and doctor's opinion.

The present invention is further illustrated in the following examples, which should not be taken to limit the scope of the invention.

EXAMPLE 1

Construction of a Gene Encoding hEGF and Angiogenin

In order to prepare hEGF gene (SEQ ID No:3), an expression vector pTED(see: Korean Patent Publication No.96-53539, KFCC-10925) was constructed by site-directed mutagenesis with an expression vector pTE105(see: FIG. 1, Korean Patent Publication No. 96-6121, KCCM-10027), and was used as source for hEGF gene.

Human angiogenin gene(SEQ ID No:1) was generated by PCR whose parameters are as follows: 30 pmoles of a primer(SEQ ID No:5) containing EcoR I restriction site and 30 pmoles of the other primer(SEQ ID No:6) containing Hind III site were added to cDNA library prepared from human liver, and subsequently mixed in Premix Top tube (Premix™-TOP, Cat#K2010, Bioneer Corp., Korea; containing 1 unit polymerase, 250 $\mu$M mixing solution, 40 $\mu$M KCl, 1.5 $\mu$M MgCl$_2$, and 50 $\mu$M Tris-HCl(pH 9.0)), then final volume was increased up to 20 $\mu$l by the addition of distilled water, and 30 $\mu$l of mineral oil was topped to prevent evaporation of the solution. DNA was amplified by 35 cycles of PCR reaction performed for 5 minutes at 94° C., 2 minutes at 58° C., 30 seconds at 72° C., 1 minute at 94° C., and finally 20 seconds at 72° C.

As a result, 380bp PCR products were obtained in which human angiogenin(SEQ ID No:1) and EcoR I and Hind III restriction sites were inserted. The PCR products were cleaved by EcoR I and Hind III and mixed with 2943bp DNA fragment resulted from ECoR I/Hind III restriction digestion of pRSETA(Invitrogen, USA) to generate cohesive ends. Two DNA fragments were ligated together by incubating with 0.5 $\mu$l of T4 DNA ligase at 16° C. for 18 hours.

Figure 2:
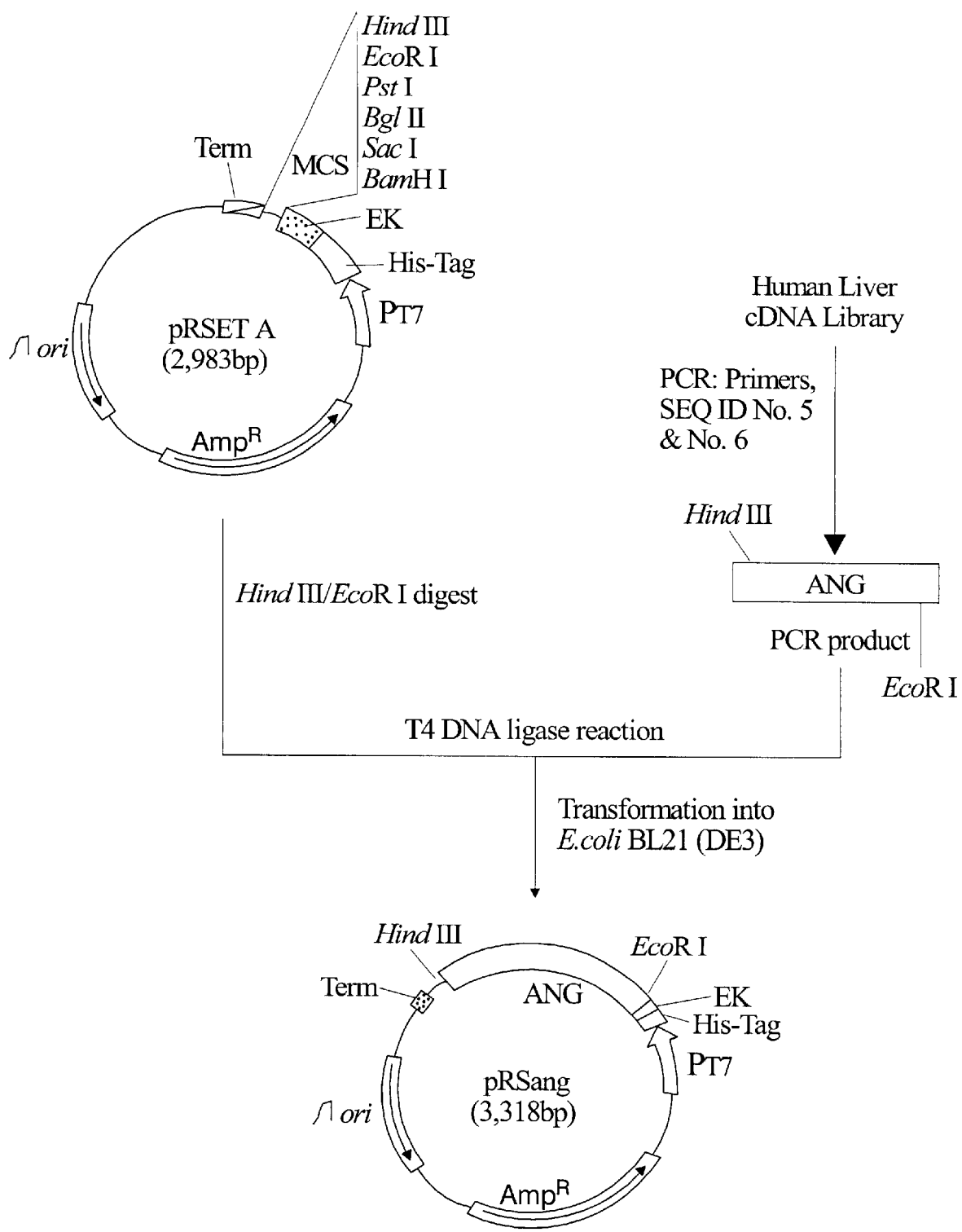
FIG. 2 is a schematic diagram depicting construction strategy of a recombinant vector pRSang.

The final plasmid was designated as pRSang and used to transform *E. coli* BL21(DE3). FIG. 2 schematically represents the construction strategy of the recombinant vector pRSang.

EXAMPLE 2

Construction of a Human Angiogenin Expression Vector pTEang

Human angiogenin gene was inserted into an expression vector pTED(KFCC-10925) obtained in Example 1 in order to express the angiogenin gene under OmpA(tac promoter) system. For PCR reaction, two primers were used: one primer(SEQ ID No:7) contains Dsa I restriction site, and the other primer(SEQ ID No:8) contains Ava I and Pst I restriction sites, converted amino acid Arg(CGC) at 122$^{nd}$ position from Arg(CGT) in angiogenin, and added Gly at 124$^{th}$ position in angiogenin. Recombinant vector pRSang was used as a template. Reaction was performed in 100 ng pRSang, 100 pM of each primer, 2 mM of each dNTP(total 8 mM), reaction solution containing Mg$^{2+}$, and 1 unit of PFU(polymerase). Final volume was increased up to 100 $\mu$l. DNA was amplified by 32 cycles at 94° C. for 1 minute, 58° C. for 1 minute, and 72° C. for 70 seconds, and then finally incubated for 5 minutes at 72° C. An amplified 391bp PCR product was separated in a 1% (w/v) agarose gel by electrophoresis, excised from the gel, purified, and then repurified following Dsa I and Pst I restriction digestion.

Figure 3:
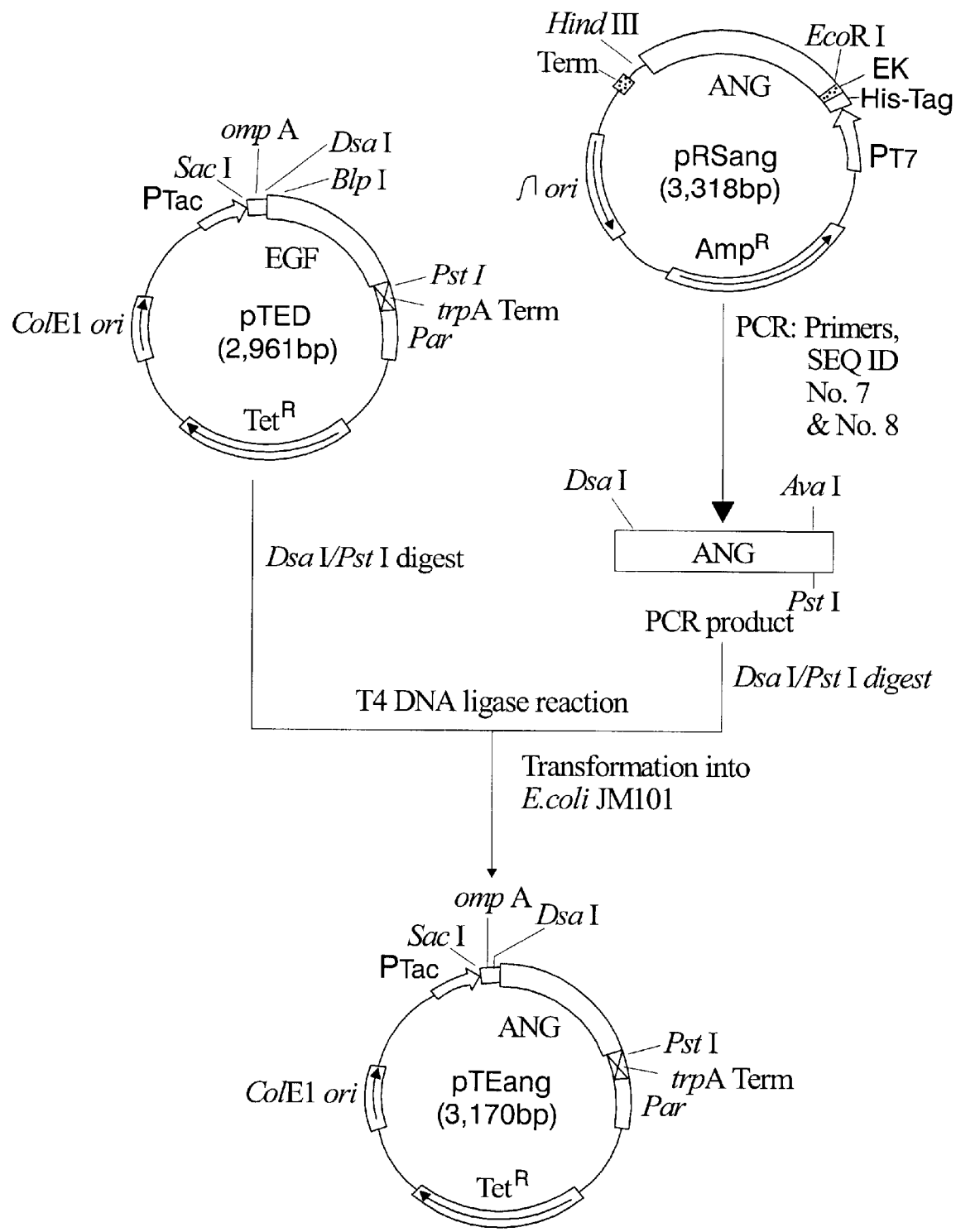
FIG. 3 is a schematic diagram depicting construction strategy of a recombinant vector pTEang.

A 391bp PCR product digested by Dsa I/Pst I was mixed with 2777bp DNA fragment prepared from plasmid vector pTED digested by Dsa I/Pst I and then purified. These two DNA fragments were ligated together by 0.5 $\mu$l of T4 ligase at 16° C. for 18 hours. The ligated plasmid was designated as pTEang and used to transform *E.coli* JM 101. In order to ensure proper insertion of angiogenin into plasmid vector pTEang, it was digested with Ava I, Sma I, and AlwN I. FIG. 3 schematically represents the construction strategy of the recombinant vector pTEang.

Angiogenin was expressed at high level in the form of inclusion body in the same way as mentioned above, except that the primer(SEQ ID No:7) was replaced with a different primer(SEQ ID No:16) containing Nde I restriction site.

EXAMPLE 3

Construction of an Expression Vector pTE4081 Containing a Fusion Gene of Angiogenin and hEGF(I)

Figure 4:
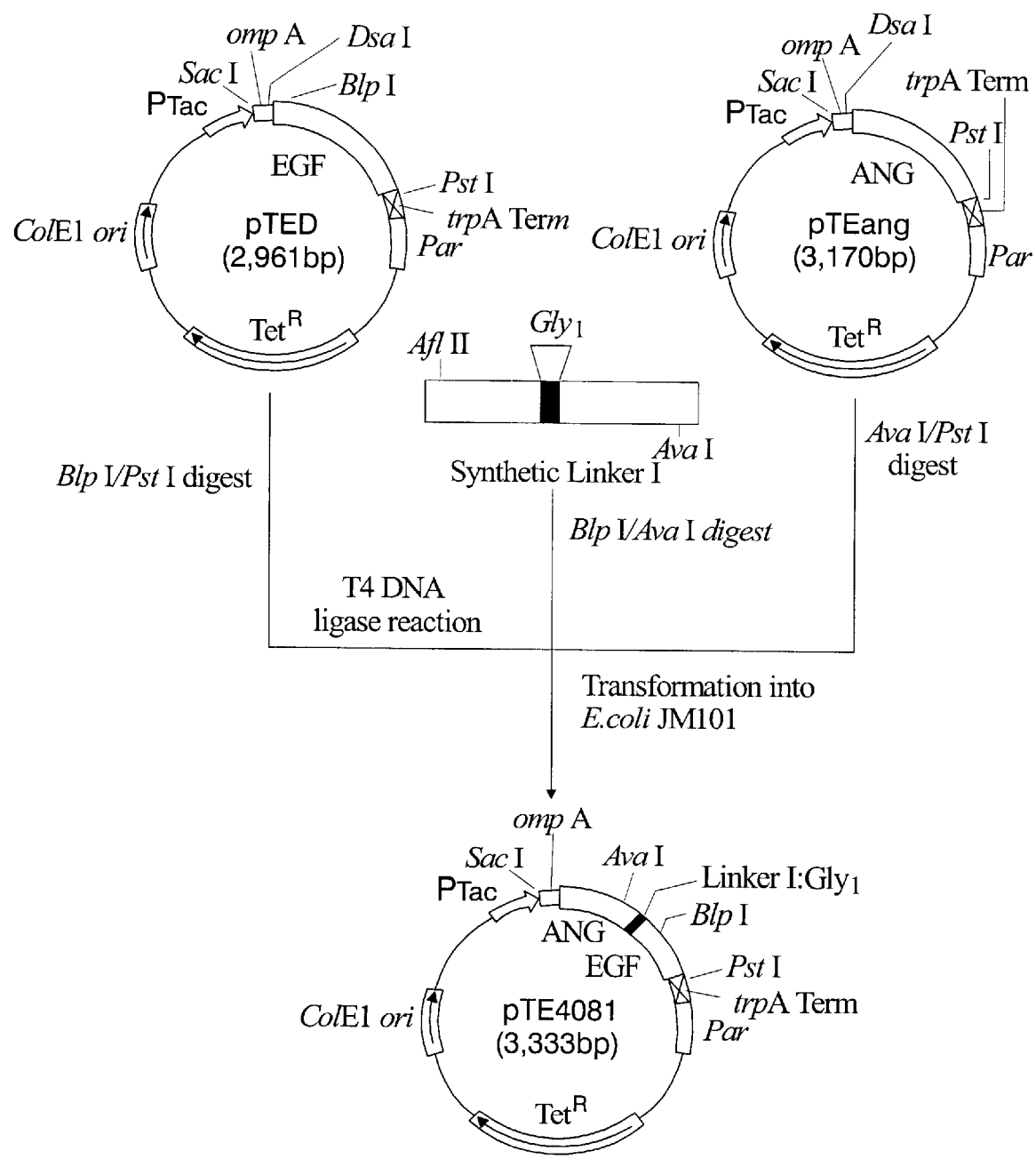
FIG. 4 is a schematic diagram depicting construction strategy of a recombinant vector pTE4081 that expresses a fusion protein of angiogenin-glycine-hEGF.

In order to construct a fusion gene of angiogenin and hEGF, an expression vector, pTE4081, containing angiogenin and EGF gene was constructed by fusing a plasmid pTED obtained in Example 1 containing EGF gene and a plasmid pTEang containing angiogenin obtained in Example 2. FIG. 4 schematically represents the construction strategy of the recombinant vector pTE4081.

More specifically, a plasmid pTED containing the EGF gene was digested by Blp I and Pst I and then separated in a 1.5%(w/v) agarose gel to obtain a 149bp DNA fragment containing the purified EGF gene. pTEang containing angiogenin was digested by Ava I and Pst I, separated in a 0.8%(w/v) agarose gel to obtain a 3156bp DNA fragment containing the purified angiogenin gene.

The linker was generated as following: 100 pmoles of one oligomer(SEQ ID No:9), 100 pmoles of the other oligomer (SEQ ID No:10), 1.5 $\mu$l of 10 nM ATP, and 15 units of T4 polynucleotide kinase were mixed and incubated for 1 hour at 37° C. and then 5 minutes at 95° C. to phosphorylate 5'-ends. Phosphorylated oligomers were annealed by heating at 95° C. for 5 minutes and slowly cooling down to 30° C. for 3 hours to generate 5'- and 3'-ends which are cohesive with Ava I and Bgl II. The phosphorylated linker was mixed with a 149bp DNA fragment containing the EGF gene and a 3156bp DNA fragment containing the angiogenin gene. Three pieces of DNA fragments were ligated together by incubating with 0.5 $\mu$l of T4 DNA ligase at 16° C. for 18 hours. This recombinant plasmid pTE4081 was used to transform *E.coli* JM 101. Proper insertion of angiogenin and EGF into the plasmid vector pTE4081 was confirmed by restriction digestion with Dsa I, AlwN I, Nsi I, and Sma I. To confirm accurate insertion, recombinant plasmid was sequenced using Sanger's dideoxynucleotide sequencing analysis(see: Molecular Cloning: A Laboratory Manual, 2nd ed. Sambrook et al., 13.6–13.10).

EXAMPLE 4

Construction of an Expression Vector pTE4082 Containing a Fusion Gene of Angiogenin and hEGF(II)

Figure 5:
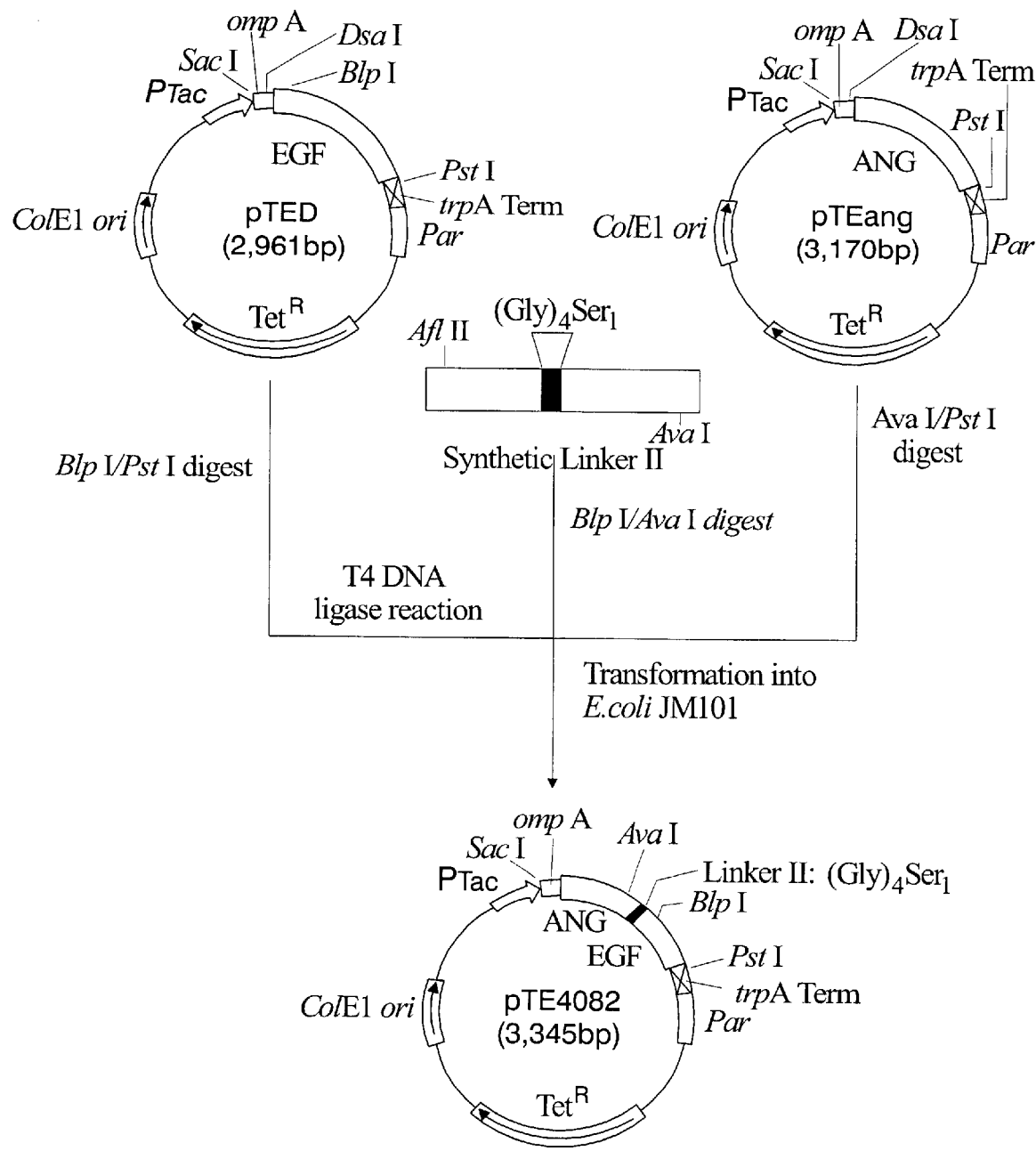
FIG. 5 is a schematic diagram depicting construction strategy of a recombinant vector pTE4082 that expresses a fusion protein of angiogenin-(glycine)$_4$ serine-hEGF.

In order to construct a fusion gene of angiogenin and hEGF, an expression vector, pTE4082, containing the angiogenin and the EGF gene was generated by fusing a DNA fragment obtained in Example 3 containing the EGF gene, a DNA fragment containing the angiogenin gene, and a linker(SEQ ID No:11 and SEQ ID No:12). FIG. 5 schematically represents the construction strategy of the recombinant vector pTE4082. Expression vector pTE4082 was constructed analogously as in Example 3, except that a different linker was used(SEQ ID No:11 and SEQ ID No:12). The accurate insertion of the genes into the expression vector was confirmed in the same way as in Example 5.

EXAMPLE 5

Construction of an Expression Vector pTE4083 Containing a Fusion Gene of Angiogenin and hEGF(III)

Figure 6:
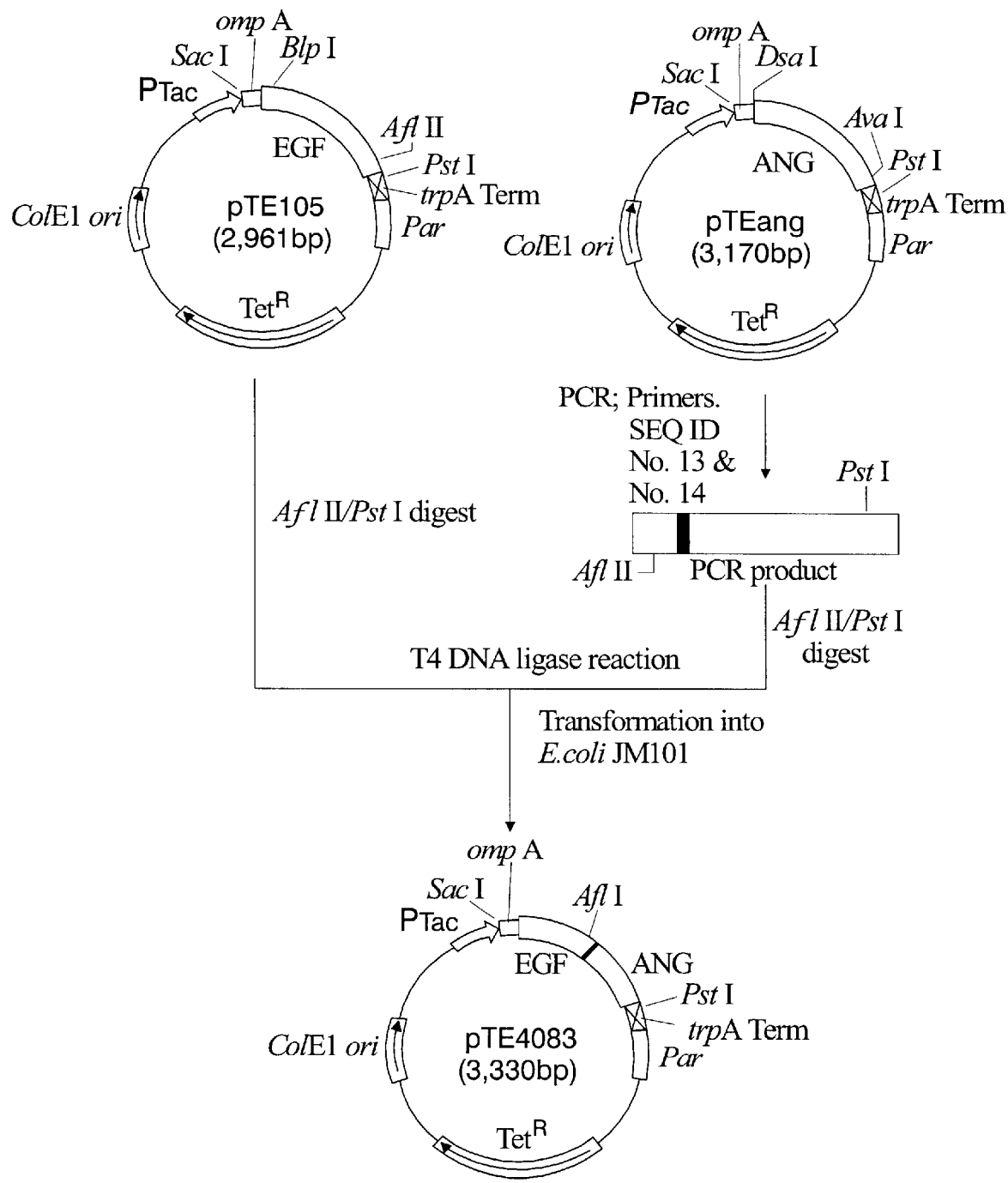
FIG. 6 is a schematic diagram depicting construction strategy of a recombinant vector pTE4083 that expresses a fusion protein of hEGF-angiogenin.

An expression vector containing a fusion gene of hEGF and angiogenin was generated by fusing a 2929bp DNA fragment obtained by Afl II/Pst I restriction digestion of pTE105 and a PCR amplified DNA fragment containing the angiogenin. For PCR reaction, pTEang was used as a template, and two primers(SEQ ID No:13 and SEQ ID No:14) were added. FIG. 6 schematically represents the construction strategy of pTE4083.

More specifically, pTE105 containing hEGF gene was digested by Afl II and Pst I, separated in a 0.8 (w/v)% agarose gel by eletrophoresis. A 2929bp fragment containing hEGF gene was excised from the gel and then purified. A PCR reaction was performed using pTEang containing the angiogenin gene as a template, a primer(SEQ ID No:13) containing Afl II site, and a primer(SEQ ID No:14) containing Pst I site. PCR reaction was performed in 100 ng of pTEang, 100 pmoles of each primer, 2 mM of each DNTP, reaction solution containing $Mg^{2+}$ and 1 unit of PFU (polymerase). Final volume was increased up to 100 µl. PCR parameters were as following: 32 cycles 94° C. for 1 minute, 58° C. for 1 minute, 72° C. for 70 seconds, and 94° C. for 30 seconds, finally incubated for 5 minutes at 72° C. An amplified 407bp PCR product containing the angiogenin gene was separated in a 1% (w/v) agarose gel, purified from the gel, and digested by Afl II and Pst I.

The aforementioned 2929bp PCR product containing hEGF gene digested by Afl II/Pst I and the 407bp PCR product containing the angiogenin gene digested by Afl II/Pst I were mixed together and then subject to ligation by incubating with 0.5 µl of T4 DNA ligase at 16° C. for 18 hours to generate pTE4083. Plasmid pTE4083 was used to transform *E.coli* JM 101. Proper insertion of the anigogenin gene and the hEGF gene into plasmid vector pTE4084 was confirmed by restriction digestion using AlwN I, BspM I, Afl II, and Pst I. Finally, accurate insertion was reconfirmed by Sanger's dideoxynucleotide sequencing analysis.

*E.coli* JM 101 transformed by plasmid pTE4083 was designated as *E.coli* JM101-plasmid pTE4083 and was deposited with Korean Culture Center of Microorganism (KCCM), an international depository located at 134 Shinchon-Dong, Seodaemun-Ku, Seoul, Korea, under an accession No. KCCM-10106 on Sep. 4, 1997.

EXAMPLE 6

Construction of an Expression Vector pTE4084 Containing a Fusion Gene of Angiogenin and hEGF(IV)

Figure 7:
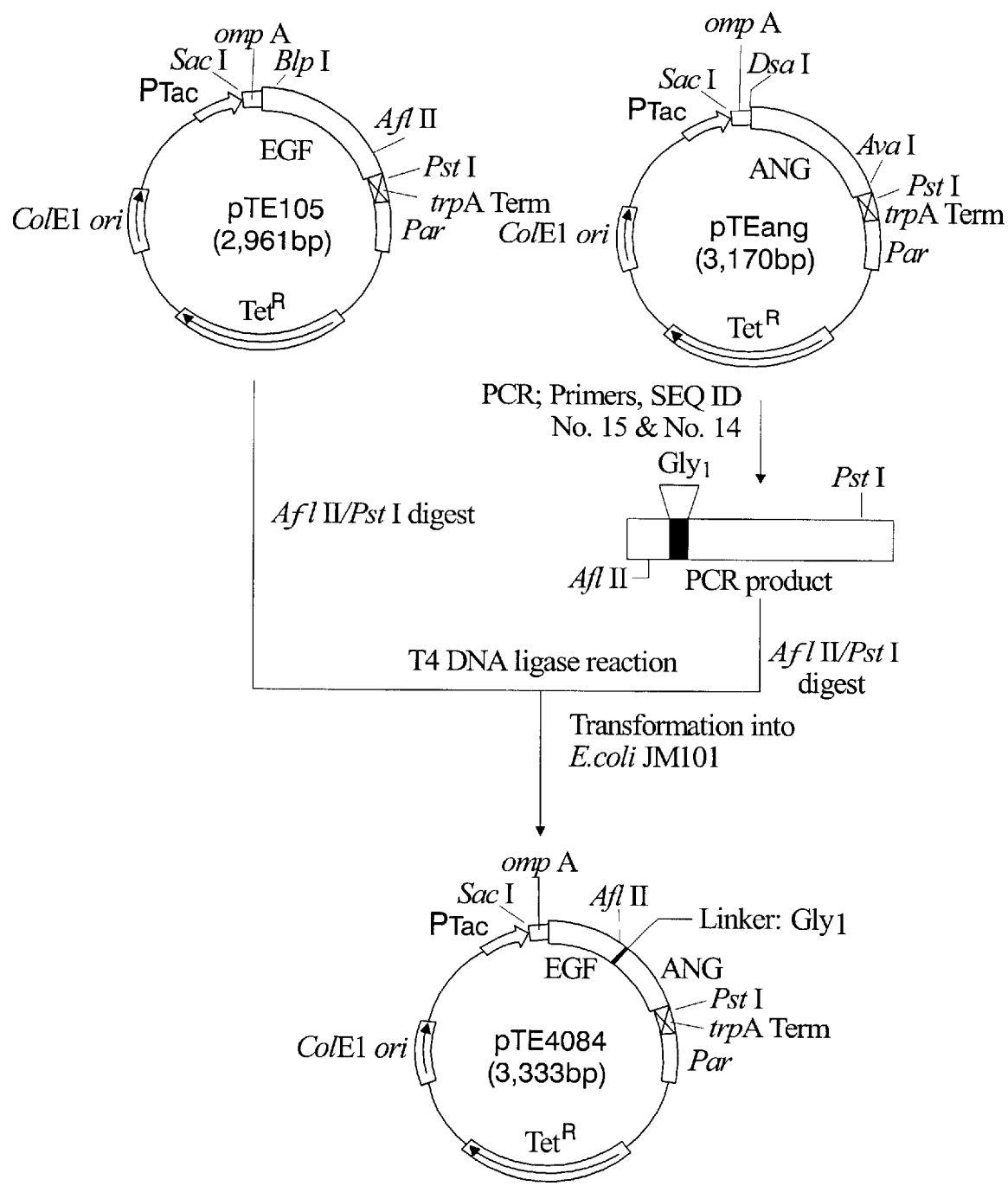
FIG. 7 is a schematic diagram depicting construction strategy of a recombinant vector pTE4084 that expresses a fusion protein of hEGF-glycine-angiogenin.

Another expression vector pTE4084 containing a fusion gene of angiogenin and hEGF was generated in a similar fashion as in Example 5 except that a 410bp DNA fragment containing the angiogenin was amplified using two primers (SEQ ID. No:14 and SEQ ID No:15). FIG. 7 schematically represents the construction strategy of recombinant vector pTE4084. Proper insertion of the genes into the vector was confirmed in the same way as in Example 5.

*E.coli* JM 101 transformed with plasmid pTE4084 was designated as *E.coli* JM101-pTE4084 and deposited with Korean Culture Center of Microorganism(KCCM), an international depositary authority located at 134 Shinchon-Dong, Seodaemun-Ku, Seoul, Korea, under an accession No. KCCM-10107 on Sep. 4, 1997.

EXAMPLE 7

Construction of an Expression Vector pTE4089 Containing a Fusion Gene of Angiogenin and hEGF(V)

Figure 8:
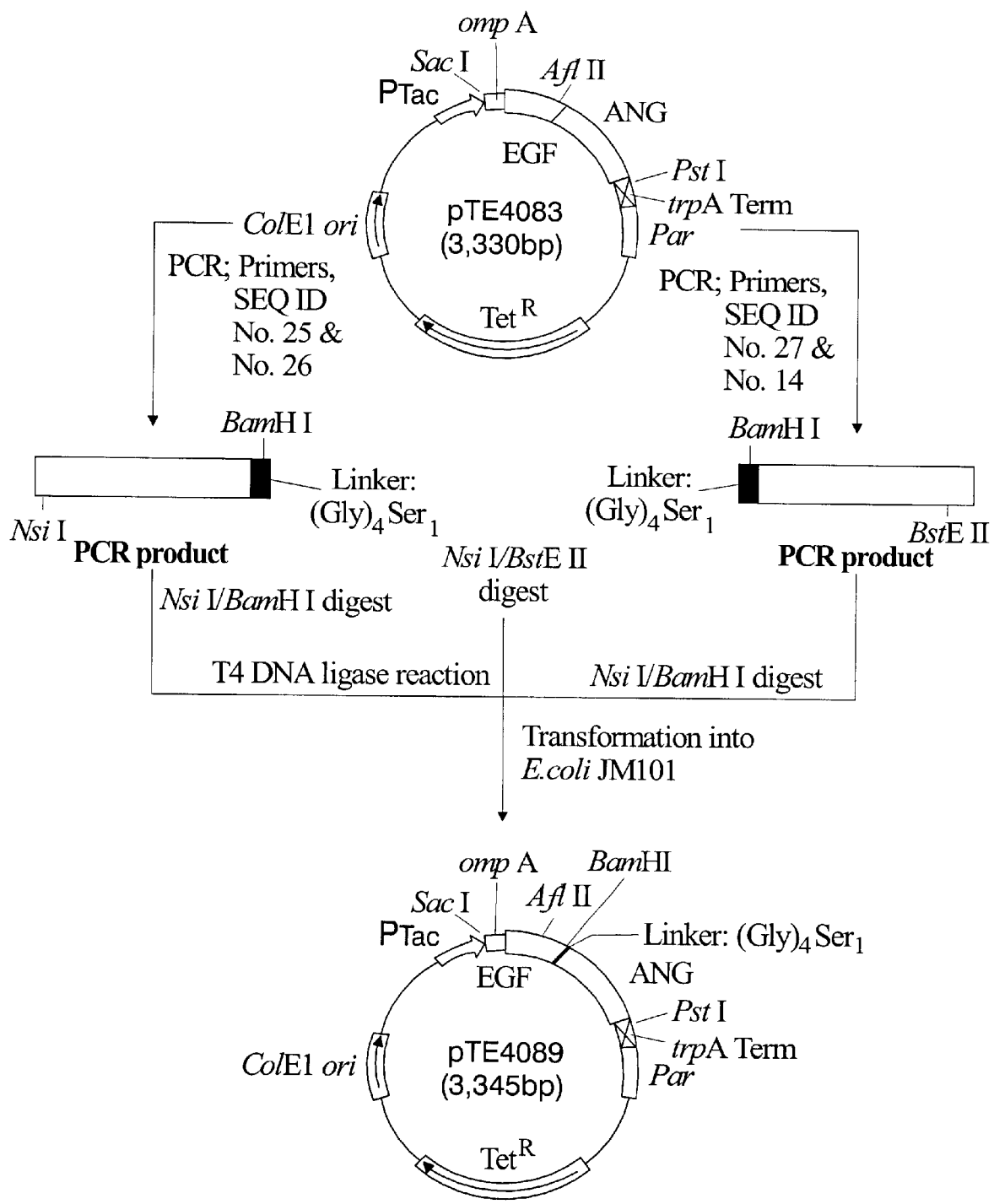
FIG. 8 is a schematic diagram depicting construction strategy of a recombinant vector pTE4089 that expresses a fusion protein of hEGF-(glycine)$_4$ serine-angiogenin.

Three pieces of DNA were ligated together to generate an expression vector pTE4089 containing a fusion gene of angiogenin and hEGF. The first 3001bp fragment contains the part of angiogenin gene and hEGF gene prepared by Nsi I/BstE II digestion of pTE4083. The second Nsi I/BamH I fragment contains a part of hEGF gene prepared by PCR amplification using pTE4083 as a template and two primers (SEQ ID No:25 and SEQ ID No:26). The last BamH I/BstE II fragment contains a part of the angiogenin gene prepared by PCR amplification using pTE4083 as a template and two primers(SEQ ID No:14 and SEQ ID No:27). FIG. 8 schematically represents the construction strategy of the recombinant vector pTE4089.

More specifically, pTE4083 containing angiogenin and hEGF was digested by Nsi I and BstE II. A 3001bp DNA fragment containing hEGF and the part of angiogenin gene was separated in a 0.8%(w/v) agarose gel.

A DNA fragment containing the part of hEGF gene was prepared by PCR amplification using pTE4083 as a template and a primer containing Nde I restriction site(SEQ ID No:25) and the other primer containing BamH I site restriction site(SEQ ID No:26). PCR reaction was performed in 100 ng of pTE4083(1 µl), 100 pmoles of each primer, 2 mM of each DNTP, reaction solution containing $Mg^{2+}$, and 1 unit of PFU(polymerase). Volume of the reaction mixture was increased up to 100 µl. The PCR mixture was preheated at 94° C. for 1 minute, and denatured at 94° C. for 30 seconds, annealed at 58° C. for 1 minute, and polymerized at 72° C. for 2 minutes. Denaturation, annealing, and polymerization were repeated 35 cycles and then finally DNA was amplified at 72° C. for 5 minutes.

A DNA fragment containing the part of the angiogenin gene was prepared by PCR reaction using a primer containing a BamH I restriction site(SEQ ID No:27) and the other primer containing a Pst I restriction site(SEQ ID No:14) in the same manner as described above. A 171bp hEGF fragment amplified by PCR and a 400bp angiogenin fragment were separated in a 1%(w/v) agarose gel, purified, and then digested by BamH I.

Both fragments were re-separated and re-purified after restriction digestion of the hEGF with Nsi I and digestion of the angiogenin with BstE II.

A 3001bp fragment containing hEGF and angiogenin, a 108bp fragment prepared by PCR reaction, and a 236bp angiogenin fragment were mixed in 0.5 µl of T4 DNA ligase and then incubated at 16° C. for 18 hours to generate pTE4089 which was used to transform *E.coli* JM 101. Proper insertion of the angiogenin and the hEGF into a plasmid vector pTE4089 was confirmed by restriction digestion with AlwN I, BspM I, BamH I, Afl II, and Pst I following electrophoresis in a 1%(w/v) agarose gel. Finally, Sanger's dideoxynucleotide sequencing analysis was used to ensure accurate insertion(see: SEQ ID No:23).

EXAMPLE 8

Construction of an Expression Vector pTE40810 Containing a Fusion Gene of Angiogenin and hEGF(VI)

Figure 9:
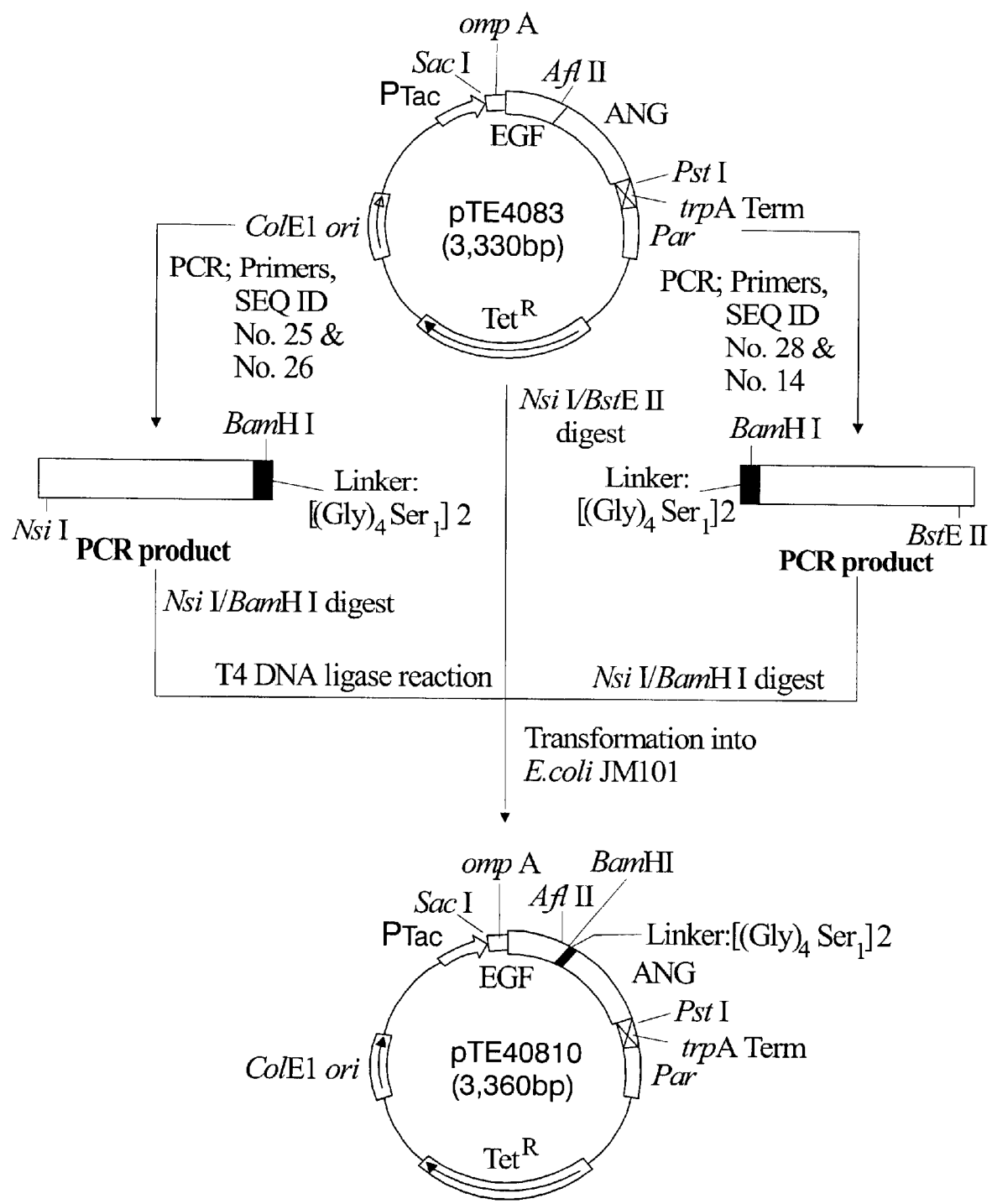
FIG. 9 is a schematic diagram depicting construction strategy of a recombinant vector pTE40810 that expresses a fusion protein of hEGF-[(glycine)$_4$ serine]$_2$-angiogenin.

Another expression vector pTE40810 containing a fusion gene of angiogenin and hEGF was prepared in the same manner as in Example 7, except that a 415bp DNA fragment was amplified using a different primer (SEQ ID No:28) and then digested by BamH I/BstE II to generate a 251bp fragment for DNA ligation. FIG. 9 schematically represents the construction strategy of a recombinant vector pTE40810. Accurate insertion of the fusion gene was confirmed in the same manner as in Example 7(see: SEQ ID No:24).

EXAMPLE 9

Construction of an Expression Vector pTE40815 Containing a Fusion Gene of Angiogenin-hEGF-angiogenin In order to generate a fusion gene of angiogenin-hEGF-angiogenin, a 3313bp vector fragment was obtained by separating Pst I/Afl II digested pTE4082 obtained in Example 4 in a 0.8%(w/v) agarose gel. A 416bp fragment of a fusion gene containing angiogenin, a linker, and 3' end of hEGF was obtained by separating Afl II/Pst I digested pTE4089 obtained from Example 7 in a 1.2%(w/v) agarose gel.

Figure 10:
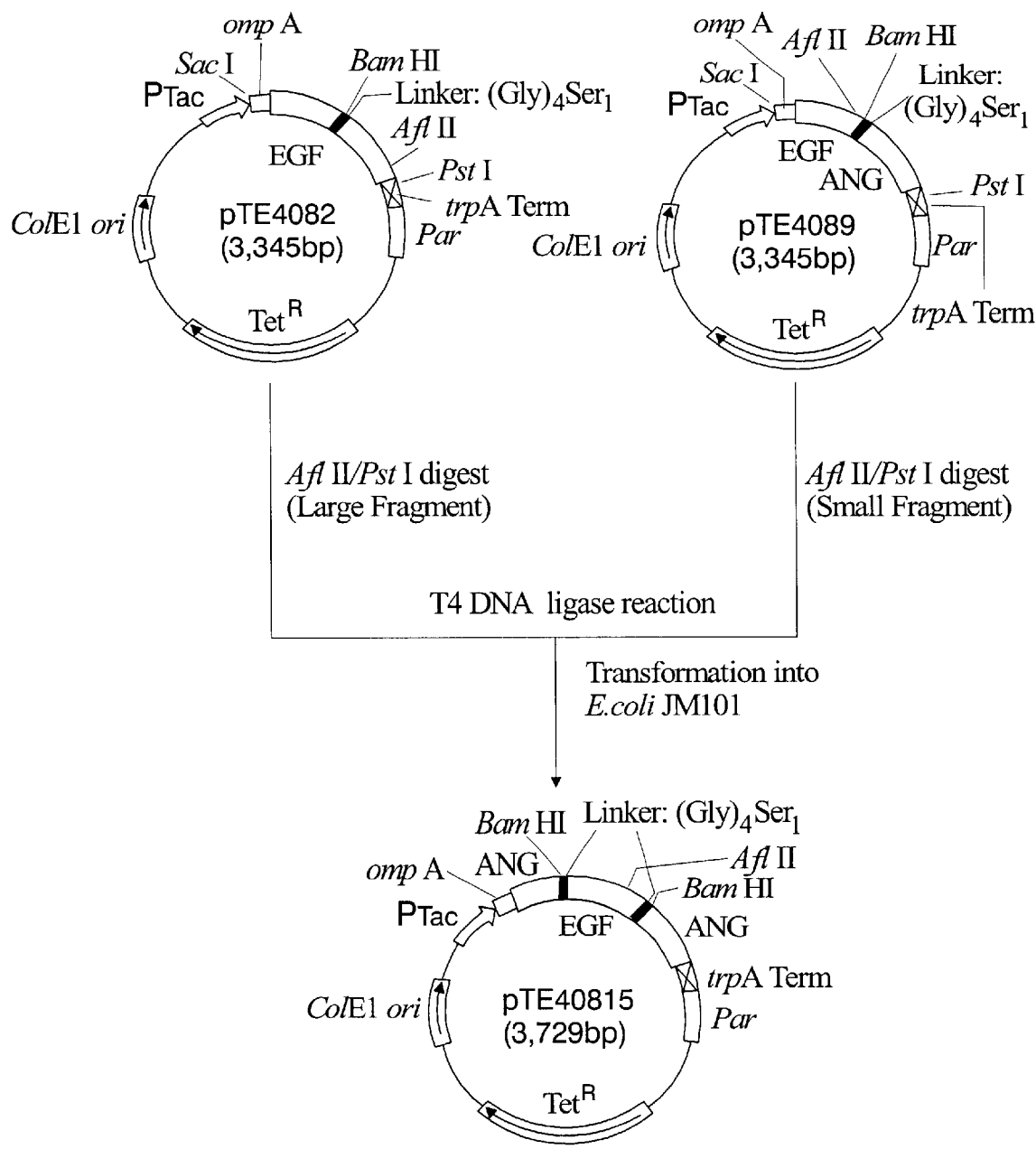
FIG. 10 is a schematic diagram depicting construction strategy of a recombinant vector pTE40815 that expresses a fusion protein of angiogenin-(glycine)$_4$ serine-hEGF-(glycine)$_4$ serine-angiogenin.

A 416bp fragment and a 3313bp fragment were mixed together and ligated by 0.5·1l of T4 DNA ligase at 16° C. for 18 hours to generate pTE40815. FIG. 10 schematically represents the construction strategy of pTE40815. A plasmid pTE40815 was used to transform E.coli JM 101. Proper insertion of a fusion gene of angiogenin-hEGF-angiogenin into a plasmid vector pTE40815 was confirmed by restriction digestion with AlwN I, BspM I, BamH I, Afl II, and Pst I. Finally, accurate insertion was confirmed by Sanger's dideoxynucleotide sequencing analysis(see: SEQ ID No:29).

EXAMPLE 10

Figure 11:
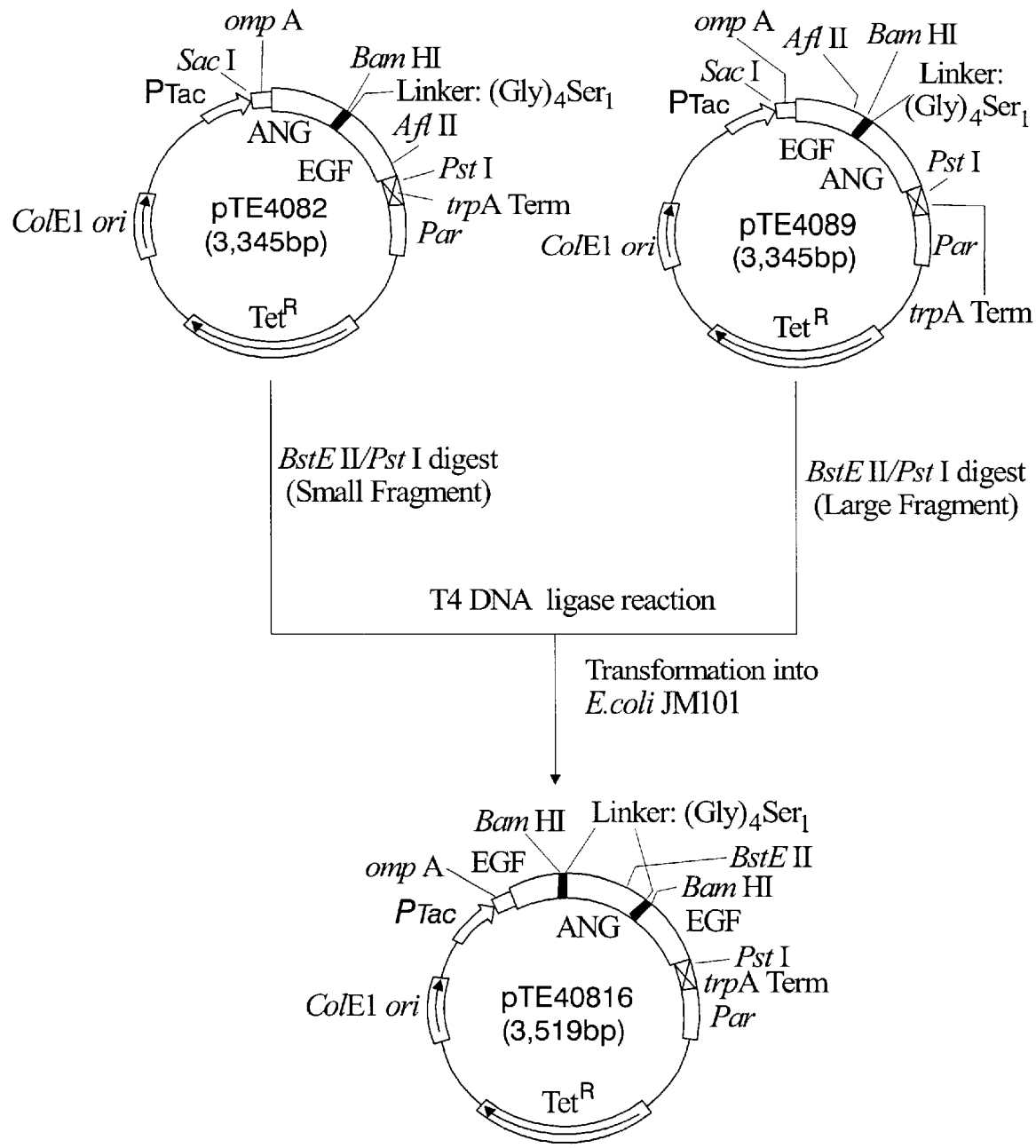
FIG. 11 is a schematic diagram depicting construction strategy of a recombinant pTE40816 that expresses a fusion protein of hEGF-(glycine)$_4$ serine-angiogenin-(glycine)$_4$ serine-hEGF.

Construction of an Expression Vector pTE40816 Containing a Fusion Gene of hEGF-angiogenin-hEGF In order to generate a fusion gene of hEGF-angiogenin-hEGF, a 3195bp vector fragment was obtained by separating Pst I/BstE II digested pTE4089 obtained in Example 7 in a 0.8%(w/v) agarose gel. A 324bp fragment of a fusion gene containing hEGF and, a linker, and 3' end of angiogenin was obtained by separating Pst I/BstE II digested pTE4082 obtained in Example 4 in a 1.2%(w/v) agarose gel. A 324bp fragment and a 3195bp fragment were mixed together and ligated by 0.5 μl of T4 DNA ligase at 16° C. for 18 hours to generate pTE40816. FIG. 11 schematically represents the construction strategy of the recombinant vector pTE40816. A plasmid pTE40816 was used to transform E.coli JM 101. Proper insertion of a fusion gene of hEGF-angiogenin-hEGF into a plasmid vector pTE40816 was confirmed by restriction digestion with AlwN I, BspM I, BamH I, Afl II, and Pst I. Finally, accurate insertion was confirmed by Sanger's dideoxynucleotide sequencing analysis(see: SEQ ID No:30).

EXAMPLE 11

Expression of a Fusion Protein of Angiogenin and hEGF in Transformed E.coli JM 101

E. coli JM 101 transformed by pTE4081, pTE4082, pTE4083, pTE4084, pTE4089, or pTE40810 which are obtained from Examples 3 to 8 was inoculated in 2 ml tetracycline-LB media and then incubated at 37° C. for 18 hours for seed culture. 2 ml of seed culture was inoculated in 100 ml of tetracycline-LB media and incubated at 37° C. When $O.D._{600}$ reached 0.7–1.0, IPTG(isopropyl β-thiogalacto-pyranoside) was added at final concentration of 1 mM to induce expression of a fusion protein. After addition of IPTG at final concentration of 1 mM, the culture was incubated for additional 20 hours. The bacterial culture was harvested by centrifugation at 7,000 g for 15 minutes at 4° C., analyzed by SDS-PAGE and Western blot using an anti-hEGF antibody and an anti-angiogenin antibody(see: FIGS. 12(A), 12(B), 13(A), and 13(B)).

Figure 12A:
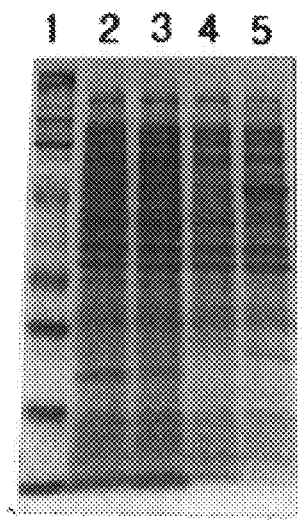
FIG. 12(A) is a photograph of bacterial culture of E.coli JM 101 transformants analyzed by SDS-PAGE technique.
Figure 12B:
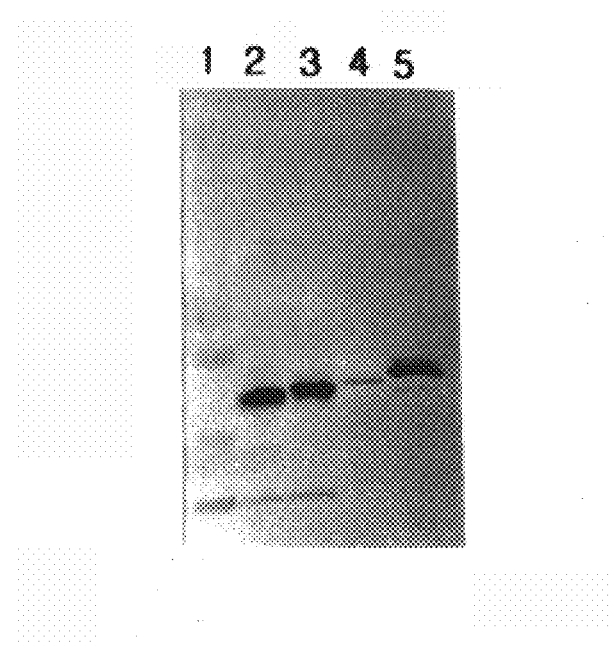
FIG. 12(B) is a photograph of Western blot analysis of FIG. 12(A).

FIG. 12(A) shows the result obtained from SDS-PAGE of the bacterial cultures of E.coli JM 101 transformed by pTE4081, pTE4082, pTE4083, or pTE4084. FIG. 12(B) shows the result obtained from the Western blot of the SDS-PAGE using an anti-hEGF antibody. In FIGS. 12(A) and 12(B), lane 1 represents molecular weight marker; lane 2, supernatant from culture of E.coli JM 101 transformed by pTE4081; lane 3, supernatant from E.coli JM 101 transformed by pTE4082; lane 4, supernatant from E.coli JM 101 transformed by pTE4083; lane 5, supernatant from E.coli JM 101 transformed by pTE4084.

Figure 13A:
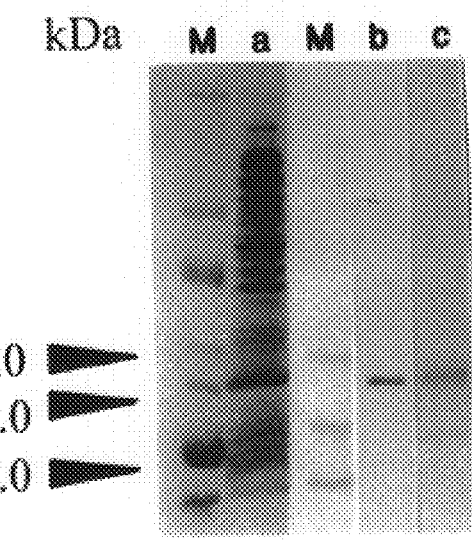
FIG. 13(A) is a photograph of SDS-PAGE and Western blot analysis of bacterial culture of E.coli JM 101 transformed by a recombinant vector pTE4089.
Figure 13B:
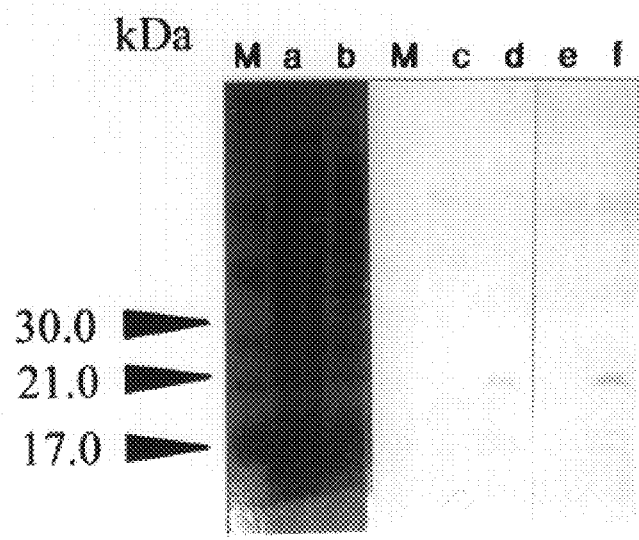
FIG. 13(B) is a photograph of SDS-PAGE and Western blot analysis of bacterial culture of E.coli JM 101 transformed by a recombinant vector pTE40810.

FIG. 13(A) shows the result of SDS-PAGE and Western blot analysis of the bacterial culture of E.coli JM 101 transformed by pTE4089. FIG. 13(B) shows the result of SDS-PAGE and Western blot analysis of bacterial culture of E.coli JM 101 transformed by pTE40810. In FIG. 13(A) lane M represents molecular weight marker; land a represents SDS-PAGE of supernatant of culture of IPTG-induced E.coli JM 101 transformant; lane b, Western blot analysis using an anti-hEGF antibody; lane c, Western blot analysis using an anti-angiogenin antibody. In FIG. 13(B) lane M represents molecular weight marker; lane a, SDS-PAGE of supernatant of E.coli JM 101 transformant prior to IPTG induction; lane b, SDS-PAGE of supernatant of E.coli JM 101 transformants after IPTG-induction; lane c and d, Western blot analysis using an anti-hEGF antibody; and, lane e and f, Western blot analysis using an anti-angiogenin antibody.

As shown in FIGS. 12(A), 12(B), 13(A), and 13(B), a fusion protein of angiogenin(SEQ ID No:2) and hEGF(SEQ ID No:4) was expressed at high level. Therefore, it is reasonable to speculate that sufficient amount of the fusion protein of angiogenin and hEGF from E.coli JM 101 transformed by pTE40815 obtained from Example 9 and pTE40816 obtained from Example 10 will be also expressed at high level.

EXAMPLE 12

Purification of a Fusion Gene and Amino Acid Sequencing

LB media was inoculated by E.coli transformed with one of the expression vectors described in Example 11, i.e., pTE4081, pTE4082, pTE4083, pTE4084, pTE4089, pTE40810, pTE40815, and pTE40816), subsequently cultured at 37° C. until O.D.$_{.600}$ reached 1.0, added IPTG at a final concentration of 1 mM to induce expression of a fusion protein, and finally cultured for additional 20 hours. The bacterial culture was harvested by centrifugation to obtain cell pellets. Cells were lysed by lysozyme or osmotic shock to obtain the protein which was subsequently separated in a 14% SDS-PAGE gel. A desired protein was confirmed by Western blot analysis. A transferred protein band was excised from a PVDF membrane and then extracted with a protein extraction kit for amino acid sequencing. More specifically, the SDS-PAGE gel was transferred onto a PVDF membrane and stained in Ponseau S. The band representing a fusion protein was excised using a razor blade to extract the protein which was used for amino acid sequencing using an amino acid sequence analyzer with a standard operation method.

SEQ ID. No:17–20, 21–22, and 31–32 were designated to the fusion proteins. SEQ ID No:17 is an amino acid sequence of a fusion protein of angiogenin-glycine-EGF expressed from pTE4081, SEQ ID No:18 is an amino acid sequence of a fusion protein of angiogenin-(glycine)$_4$serine-EGF expressed from pTE4082, SEQ ID No:19 is an amino acid sequence of a fusion protein of EGF-angiogenin expressed from pTE4083, SEQ ID No:20 is an amino acid sequence of a fusion protein of EGF-glycine-angiogenin expressed from pTE4084, SEQ ID No:21 is an amino acid sequence of a fusion protein of EGF-(glycine)$_4$serine-angiogenin expressed from pTE4089, SEQ ID No:22 is an amino acid sequence of a fusion proteins of EGF[(glycine)$_4$serine]$_2$-angiogenin expressed from pTE40810, SEQ ID No:31 is an amino acid sequence of a fusion protein of angiogenin-(glycine)$_4$serine-EGF-(glycine)$_4$serine-angiogenin expressed from pTE40815, and SEQ ID No:32 is an amino acid sequence of a fusion protein of EGF-(glycine)$_4$ serine-angiogenin-(glycine) 4 serine-EGF expressed from pTE40816

A sample containing EGF-(glycine)$_4$ serine-angiogenin was subject to heparin-Sepharose column chromatography (heparin-Sepharose CL-4B, Pharmacia Biotech. Inc., USA) to elute the bound proteins with a phosphate buffer containing 1M NaCl. The fractions were pooled and subject to DEAE-Sephadex column chromatography(DEAE-Sephadex A-25, Pharmacia Biotech. Inc., USA) and purified proteins attached to resins in phosphate buffer containing 0.4–0.7M NaCl to measure receptor binding activities and tRNase activities.

EXAMPLE 13

Receptor Binding Activity of a Fusion Protein

Binding activity of a fusion protein was measured by competitive binding between a sample and EGF labelled with an isotope, where $^{125}$I-EGF and the sample were added together to A431 cells(ATCC: CRL-1555) that express EGF receptors at high level on the cell surface. More specifically, A431 cells were plated on 24 well plates at 4×10$^4$ cells/ml, cultured until the cells reached confluency, and then fixed in 10%(v/v) formaldehyde. Subsequently, 20 µl of each $^{125}$I-labelled EGF and the sample solution was added to each well to bind to the receptors competitively. Unbound EGF was washed out and cells were detached from the wells to count the radioactivity with a γ-counter. Cpm value was converted to % binding activity and standard curve was obtained with the concentration of control and % binding activity. Binding activity of the sample was decided by substituting % binding activity of the sample to the standard curve and compared with the binding activity of EGF(see: Table 1).

TABLE 1

Receptor Binding Activities of the fusion proteins

| Sample | Binding Activity (%) |
|---|---|
| hEGF | 100 |
| Angiogenin-glycine-hEGF | 92.5 |
| Angiogenin-(glycine)$_4$serine-hEGF | 96.4 |
| hEGF-angiogenin | 98.0 |
| hEGF-glycine-angiogenin | 106.6 |
| hEGF-(glycine)$_4$serine-angiogenin | 102.2 |
| hEGF-[(glycine)$_4$serine]$_2$-angiogenin | 95.6 |
| hEGF-(glycine)$_4$serine-angiogenin-(glycine)$_4$serine-hEGF | 108.5 |
| Angiogenin-(glycine)$_4$serine-hEGF-(glycine)$_4$serine-angiogenin | 93.3 |

As demonstrated in Table 1, binding activity of the fusion protein to hEGF receptors is more than 90% and it is not much different from that of EGF.

EXAMPLE 14

RNase Activity of Fusion Protein

50 µl of sample containing a fusion protein was mixed with 50 µl of yeast t-RNA mixture containing reaction buffer composed of 120 mM HEPES, 120 mM NaCl, 0.004% BSA and incubated at 37° C. for 2 hours. Reaction was interrupted by an equal volume of 6% perchloric acid. Subsequently, the reaction mixture was centrifuged for 10 minutes and used to measure optical density at 260 nm from which the standard curve was made to measure RNase activity. Activities of the samples were compared with that of angiogenin(see: Table 2).

TABLE 2

RNase activities of the fusion proteins

| Sample | RNase Activity(%) |
|---|---|
| Angiogenin | 100 |
| Angiogenin-glycine-hEGF | 25–34 |
| Angiogenin-(glycine)$_4$serine-hEGF | 36–45 |
| hEGF-angiogenin | 65–90 |
| hEGF-glycine-angiogenin | 69–85 |
| hEGF-(glycine)$_4$serine-angiogenin | 80–107 |
| hEGF-[(glycine)$_4$serine]$_2$-angiogenin | 85–121 |
| hEGF-(glycine)$_4$serine-angiogenin-(glycine)$_4$serine-hEGF | 43–72 |
| Angiogenin-(glycine)$_4$serine-hEGF-(glycine)$_4$serine-angiogenin | 80–127 |

As clearly demonstrated in Table 2, RNase activities of the fusion proteins are improved as the length of a linker increases.

EXAMPLE 15

Cytotoxicity of a Fusion Protein to Cancer Cells In Vitro

In order to evaluate activity of the fusion protein in vitro, breast cancer cell line, MCF-7(ATCC-HTB22), was cultured in DMEM supplemented with 10% FBS. Cells were plated on 96-well plates at 1×10$^4$ cells/ml and cultured for 1 day. Medium was replaced with serum free-media containing control, sample, and 5-fluorouracil(for comparison) and cultured for 2 days, survival rate was measured with MTT (3-(3,4-dimethylthiazol-2-yl)-2,5-diphenyltetrazolium bromide), and $IC_{50}$ was calculated(see: Table 3).

TABLE 3

Cytotoxicity of the fusion proteins to breast cancer cells

| Sample | $IC_{50}$ (nM) |
|---|---|
| hEGF | >100 |
| Angiogenin | >100 |
| Angiogenin-glycine-hEGF | >50 |
| Angiogenin-(glycine)$_4$serine-hEGF | >50 |
| hEGF-angiogenin | 48.0 |
| hEGF-glycine-angiogenin | 12.5 |
| hEGF-(glycine)$_4$serine-angiogenin | 6.2 |
| hEGF-[(glycine)$_4$serine]$_2$-angiogenin | 6.2 |
| hEGF-(glycine)$_4$serine-angiogenin-(glycine)$_4$serine-hEGF | >50 |
| Angiogenin-(glycine)$_4$serine-hEGF-(glycine)$_4$serine-angiogenin | 12.5 |
| 5-fluorouracil | 47.1 |

As clearly demonstrated in Table 3, the fusion proteins are proven to be effective in leading the cancer cells to death.

EXAMPLE 16

Toxicity of a Fusion Protein

In order to evaluate cytotoxicity of the fusion protein in vitro, CHO-K1 (ATCC-CCL61) cells which do not express hEGF receptors were cultured in F-12 medium supplemented with 10% FBS. Cells were cultured on 96 well plates at $1 \times 10^4$ cells/ml for 1 day, and received serum-free media containing control and samples, and incubated for additional 2 days. Survival rate of the cells was measured with MTT, in an analogous manner as in Example 15(see: Table 4).

TABLE 4

Cytotoxicities of the fusion proteins to CHO-K1 cells

| Sample | $IC_{50}$ (nM) |
|---|---|
| hEGF | >100 |
| Angiogenin | >100 |
| Angiogenin-glycine-hEGF | >100 |
| Angiogenin-(glycine)$_4$serine-hEGF | >100 |
| hEGF-angiogenin | >100 |
| hEGF-glycine-angiogenin | >100 |
| hEGF-(glycine)$_4$serine-angiogenin | >100 |
| hEGF-[(glycine)$_4$serine]$_2$-angiogenin | >100 |
| hEGF-(glycine)$_4$serine-angiogenin-(glycine)$_4$serine-hEGF | >100 |
| Angiogenin-(glycine)$_4$serine-hEGF-(glycine)$_4$serine-angiogenin | >100 |
| 5-fluorouracil | 49.5 |

As clearly demonstrated in Table 4, the fusion proteins exhibit no toxicity to the cells that do not express hEGF receptors.

EXAMPLE 17

Anticancer Effect of a Toxic Fusion Protein In Vivo

To evaluate anticancer activity of the fusion protein in vivo, A431 cultured cells were transferred subcutaneously to the abdominal region of an immunodeficient nude mouse (20–25 g body weight) at $2 \times 10^7$ in 0.2 ml. When the proper size of tumor was formed, tumor was removed from the mouse under sterilization condition and cut into pieces of 2–3 mm to be transferred subcutaneously with a troca. When the size of the transplanted tumor of the nude mouse reached 80 ml, mice were divided into 5 groups(6 mice in one group) for i.v. injection. 100 μg/kg body weight of the fusion protein and angiogenin were administered by i.v. injection every 3 day for 4 weeks. After final administration, the area of the tumor-surface was measured by vernier calipers.

Figure 14A:
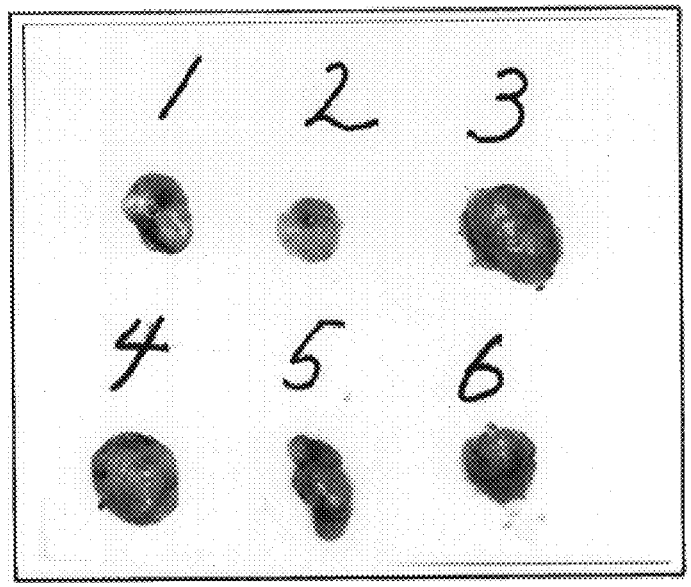
FIG. 14(A) is a photograph showing the size of the tumors in control mice.
Figure 14B:
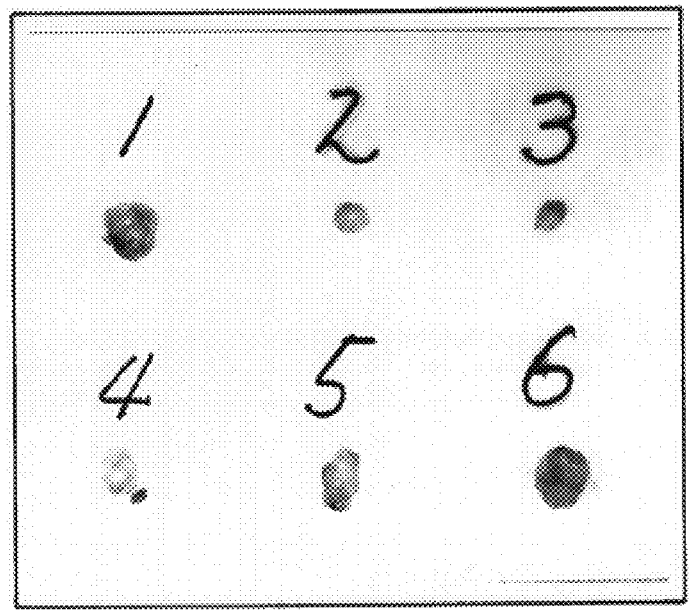
FIG. 14(B) is a photograph showing the size of the tumors in mice injected with hEGF-(glycine)$_4$ serine-angiogenin.

The tumor cells were excised after 4 weeks and measured for the weight(see: Table 5). FIG. 14 (A) and FIG. 14(B) are photographs showing the size of the tumors from mice injected with PBS(phosphate buffered saline) and hEGF-(glycine)$_4$serine-angiogenin, respectively, where each number indicates the tumor taken from the mouse sacrificed at 3 day interval after final administration.

TABLE 5

Anticancer effects of the fusion proteins in vivo

| Sample | Mean tumor-surface (unit: mm$^2$) | | | Mean tumor weight (unit: g) |
|---|---|---|---|---|
| | A | B | B/A | |
| Control | 78.5 ± 3.6 | 482.4 ± 10.4 | 6.1 | 4.8 ± 0.2 |
| Angiogenin | 79.3 ± 2.1 | 477.2 ± 6.7 | 6.0 | 5.0 ± 0.7 |
| hEGF-glycine-angiogenin | 79.7 ± 6.0 | 417.5 ± 5.2 | 5.2 | 3.7 ± 0.6 |
| hEGF-(glycine)$_4$serine-angiogenin | 78.7 ± 2.7 | 206.0 ± 4.6 | 2.6 | 2.0 ± 0.3 |
| hEGF-[(glycine)$_4$serine]$_2$-angiogenin | 77.9 ± 6.2 | 217.7 ± 5.1 | 2.8 | 2.4 ± 0.4 |

A Mean tumor-surface on the day of administration
B Mean tumor-surface after 4 weeks As clearly demonstrated in Table 5, growth of tumors in the mice received the fusion proteins was dramatically inhibited in comparison with that of tumors in mice received angiogenin only. Death or symptoms caused by side effects was not observed while inhibitory effect on tumor growth was observed even with naked eyes.

Acute Toxicity Test

Acute toxicity test was performed to confirm low toxicity of the fusion protein of the present invention: the fusion protein generated in the Example described as above 'EGF-(glycine)$_4$serine-anigiogenin' was injected in the abdominal region of male mice(ICR mouse, 20–25 g body weight, 5 mice in one group) at 0.1 to 100 mg/kg. Subsequently, the mice were caged and observed for general symptoms. After 7 days, the number of the dead mice was counted. However, median lethal dose($LD_{50}$, mg/kg) was not measurable since only 1 mouse died in the group that received 100 mg/kg. As a result, it is obvious that toxicity of the fusion protein is strikingly low since $LD_{50}$ is much higher than 100 mg/kg.

As clearly illustrated and demonstrated as aboves, the present invention provides a fusion protein which is superior to the conventional fusion proteins used as anticancer agents, in light of the following points: first, it overcomes immunotoxicity issue since the human-derived protein components do not induce antibody formation; second, it selectively kills the cancer cells with difference of 1000 fold in $IC_{50}$ in spite of its low molecular weight, though each component itself does not have activity to the cancer cells. Therefore, the fusion protein of the invention may be practically applied for treatment of the tumors that express hEGF receptors at high level.

What is claimed is:

1. A fusion protein consisting of human epidermal growth factor, a linker composed of 0 to 20 amino acids, and human angiogenin in a sequential order.

2. The fusion protein of claim 1, wherein the human epidermal growth factor and the human angiogenin are fused in a molecular ratio of 1:0.5–2.

3. The fusion protein of claim 1, wherein the linker is selected from the group consisting of glycine, (glycine)$_4$serine, and [(glycine)$_4$serine]$_2$.

4. A nucleic acid molecule encoding the fusion protein of claim 1.

5. An expression vector containing the nucleic acid molecule of claim 4.

6. A microorganism transformed by the expression vector of claim 5.

7. A process for preparing a fusion protein comprising the steps of: inducing expression of the fusion protein from the microorganism of claim 6 and obtaining the recombinant fusion protein.

8. A fusion protein produced by the process of claim 7.

9. An anticancer agent comprising the fusion protein of claim 1 as an active ingredient and pharmaceutically acceptable carriers.

10. A fusion protein consisting of human epidermal growth factor, a linker of [(glycine)$_4$serine]$_2$ and human angiogenin, which is represented as SEQ ID No: 22.

11. A nucleic acid molecule encoding the fusion protein of claim 10, which is represented as SEQ ID No: 24.

12. An expression vector pTE40810 containing the nucleic acid molecule of claim 11.

* * * * *

UNITED STATES PATENT AND TRADEMARK OFFICE
CERTIFICATE OF CORRECTION

PATENT NO.    : 6,541,619 B1
DATED         : April 1, 2003
INVENTOR(S)   : Myung-Hwan Park It is certified that error appears in the above-identified patent and that said Letters Patent is hereby corrected as shown below:

<u>Title page,</u>
Item [75], Inventors, delete "Byung-Kwon Oh" and substitute with
-- Oh-Byung Kwon --

Signed and Sealed this

Seventh Day of October, 2003

JAMES E. ROGAN
*Director of the United States Patent and Trademark Office*

SEQUENCE LISTING

<160> NUMBER OF SEQ ID NOS: 32

<210> SEQ ID NO 1
<211> LENGTH: 369
<212> TYPE: DNA
<213> ORGANISM: Homo sapiens

<400> SEQUENCE: 1

```
caggataact ccaggtacac acacttcctg acccagcact atgatgccaa accacagggc        60
cgggatgaca gatactgtga agcatcatg aggagacggg gcctgacctc accctgcaaa        120
gacatcaaca catttattca tggcaacaag cgcagcatca aggccatctg tgaaaacaag       180
aatggaaacc ctcacagaga aaacctaaga ataagcaagt cttctttcca ggtcaccact       240
tgcaagctac atggaggttc cccctggcct ccatgccagt accgagccac agcgggttc        300 agaaacgttg ttgttgcttg tgaaaatggc ttacctgtcc acttggatca gtcaattttc       360
cgtcgtccg                                                                369
```

<210> SEQ ID NO 2
<211> LENGTH: 123
<212> TYPE: PRT
<213> ORGANISM: Homo sapiens

<400> SEQUENCE: 2

```
Gln Asp Asn Ser Arg Tyr Thr His Phe Leu Thr Gln His Tyr Asp Ala
 1               5                  10                  15

Lys Pro Gln Gly Arg Asp Asp Arg Tyr Cys Glu Ser Ile Met Arg Arg
            20                  25                  30

Arg Gly Leu Thr Ser Pro Cys Lys Asp Ile Asn Thr Phe Ile His Gly
        35                  40                  45

Asn Lys Arg Ser Ile Lys Ala Ile Cys Glu Asn Lys Asn Gly Asn Pro
    50                  55                  60

His Arg Glu Asn Leu Arg Ile Ser Lys Ser Ser Phe Gln Val Thr Thr
65                  70                  75                  80

Cys Lys Leu His Gly Gly Ser Pro Trp Pro Pro Cys Gln Tyr Arg Ala
                85                  90                  95

Thr Ala Gly Phe Arg Asn Val Val Val Ala Cys Glu Asn Gly Leu Pro
            100                 105                 110

Val His Leu Asp Gln Ser Ile Phe Arg Arg Pro
        115                 120
```

<210> SEQ ID NO 3
<211> LENGTH: 159
<212> TYPE: DNA
<213> ORGANISM: Homo sapiens

<400> SEQUENCE: 3

```
aatagtgact ccgaatgccc gctgagccat gacggctact gcctgcacga cggcgtatgc        60
atgtacatcg aagcactgga caaatacgcg tgcaactgtg ttgttggcta catcggcgag       120
cgctgtcagt accgtgacct taagtggtgg gaactgcgc                              159
```

<210> SEQ ID NO 4
<211> LENGTH: 53
<212> TYPE: PRT
<213> ORGANISM: Homo sapiens

<400> SEQUENCE: 4

```
Asn Ser Asp Ser Glu Cys Pro Leu Ser His Asp Gly Tyr Cys Leu His
 1               5                  10                 15
Asp Gly Val Cys Met Tyr Ile Glu Ala Leu Asp Lys Tyr Ala Cys Asn
             20                  25                  30
Cys Val Val Gly Tyr Ile Gly Glu Arg Cys Gln Tyr Arg Asp Leu Lys
         35                  40                  45
Trp Trp Glu Leu Arg
     50
```

```
<210> SEQ ID NO 5
<211> LENGTH: 27
<212> TYPE: DNA
<213> ORGANISM: Artificial Sequence
<220> FEATURE:
<223> OTHER INFORMATION: primer for human angiogenin

<400> SEQUENCE: 5
agaattcagg ataactccag gtacaca                                    27

<210> SEQ ID NO 6
<211> LENGTH: 27
<212> TYPE: DNA
<213> ORGANISM: Artificial Sequence
<220> FEATURE:
<223> OTHER INFORMATION: primer for human angiogenin

<400> SEQUENCE: 6
taagcttacg gaaaattgac tgatcca                                    27

<210> SEQ ID NO 7
<211> LENGTH: 33
<212> TYPE: DNA
<213> ORGANISM: Artificial Sequence
<220> FEATURE:
<223> OTHER INFORMATION: primer for human angiogenin

<400> SEQUENCE: 7
aaccgtggcg caggcccagg ataactccag gta                             33

<210> SEQ ID NO 8
<211> LENGTH: 33
<212> TYPE: DNA
<213> ORGANISM: Artificial Sequence
<220> FEATURE:
<223> OTHER INFORMATION: primer for human angiogenin

<400> SEQUENCE: 8
gcctgcagtt agcccgggcg acggaaaatt gac                             33

<210> SEQ ID NO 9
<211> LENGTH: 28
<212> TYPE: DNA
<213> ORGANISM: Artificial Sequence
<220> FEATURE:
<223> OTHER INFORMATION: linker for ligating angiogenin and hEGF

<400> SEQUENCE: 9
ccgggcaata gtgactccga atgtccgc                                   28

<210> SEQ ID NO 10
<211> LENGTH: 27
<212> TYPE: DNA
<213> ORGANISM: Artificial Sequence
<220> FEATURE:
```

```
<223> OTHER INFORMATION: oligomer for linker

<400> SEQUENCE: 10
tcagcggaca ttcggagtca ctattgc                                           27

<210> SEQ ID NO 11
<211> LENGTH: 40
<212> TYPE: DNA
<213> ORGANISM: Artificial Sequence
<220> FEATURE:
<223> OTHER INFORMATION: linker for expression vector pTE4082

<400> SEQUENCE: 11
ccgggcggcg gcggatccaa tagtgactcc gaatgtccgc                             40

<210> SEQ ID NO 12
<211> LENGTH: 39
<212> TYPE: DNA
<213> ORGANISM: Artificial Sequence
<220> FEATURE:
<223> OTHER INFORMATION: linker for expression vector pTE4082

<400> SEQUENCE: 12
tcagcggaca ttcggagtca ctattggatc cgccgccgc                              39

<210> SEQ ID NO 13
<211> LENGTH: 37
<212> TYPE: DNA
<213> ORGANISM: Artificial Sequence
<220> FEATURE:
<223> OTHER INFORMATION: primer for 2929bp fragment of hEGF gene

<400> SEQUENCE: 13
acttaagtgg tgggaactgc gccaggataa ctccagg                                37

<210> SEQ ID NO 14
<211> LENGTH: 30
<212> TYPE: DNA
<213> ORGANISM: Artificial Sequence
<220> FEATURE:
<223> OTHER INFORMATION: primer for 2929bp of hEGF and 410bp fragment
      of angiogenin

<400> SEQUENCE: 14
gcctgcaggt tatcacgggc gacggaaaat                                        30

<210> SEQ ID NO 15
<211> LENGTH: 40
<212> TYPE: DNA
<213> ORGANISM: Artificial Sequence
<220> FEATURE:
<223> OTHER INFORMATION: primer for 410bp fragment of angiogenin

<400> SEQUENCE: 15
acttaagtgg tgggaactgc gcggccagga taactccagg                             40

<210> SEQ ID NO 16
<211> LENGTH: 33
<212> TYPE: DNA
<213> ORGANISM: Artificial Sequence
<220> FEATURE:
<223> OTHER INFORMATION: primer containing NdeI restriction site

<400> SEQUENCE: 16
gcgcacatat gcaggataac tccaggtaca cac                                    33
```

```
<210> SEQ ID NO 17
<211> LENGTH: 177
<212> TYPE: PRT
<213> ORGANISM: Artificial Sequence
<220> FEATURE:
<223> OTHER INFORMATION: amino acid sequence of fusion protein

<400> SEQUENCE: 17
```

Gln Asp Asn Ser Arg Tyr Thr His Phe Leu Thr Gln His Tyr Asp Ala
 1               5                  10                  15

Lys Pro Gln Gly Arg Asp Asp Arg Tyr Cys Glu Ser Ile Met Arg Arg
            20                  25                  30

Arg Gly Leu Thr Ser Pro Cys Lys Asp Ile Asn Thr Phe Ile His Gly
        35                  40                  45

Asn Lys Arg Ser Ile Lys Ala Ile Cys Glu Asn Lys Asn Gly Asn Pro
 50                  55                  60

His Arg Glu Asn Leu Arg Ile Ser Lys Ser Ser Phe Gln Val Thr Thr
 65                  70                  75                  80

Cys Lys Leu His Gly Gly Ser Pro Trp Pro Pro Cys Gln Tyr Arg Ala
                85                  90                  95

Thr Ala Gly Phe Arg Asn Val Val Val Ala Cys Glu Asn Gly Leu Pro
            100                 105                 110

Val His Leu Asp Gln Ser Ile Phe Arg Arg Pro Gly Asn Ser Asp Ser
        115                 120                 125

Glu Cys Pro Leu Ser His Asp Gly Tyr Cys Leu His Asp Gly Val Cys
130                 135                 140

Met Tyr Ile Glu Ala Leu Asp Lys Tyr Ala Cys Asn Cys Val Val Gly
145                 150                 155                 160

Tyr Ile Gly Glu Arg Cys Gln Tyr Arg Asp Leu Lys Trp Trp Glu Leu
                165                 170                 175

Arg

```
<210> SEQ ID NO 18
<211> LENGTH: 181
<212> TYPE: PRT
<213> ORGANISM: Artificial Sequence
<220> FEATURE:
<223> OTHER INFORMATION: amino acid sequence of fusion protein

<400> SEQUENCE: 18
```

Gln Asp Asn Ser Arg Tyr Thr His Phe Leu Thr Gln His Tyr Asp Ala
 1               5                  10                  15

Lys Pro Gln Gly Arg Asp Asp Arg Tyr Cys Glu Ser Ile Met Arg Arg
            20                  25                  30

Arg Gly Leu Thr Ser Pro Cys Lys Asp Ile Asn Thr Phe Ile His Gly
        35                  40                  45

Asn Lys Arg Ser Ile Lys Ala Ile Cys Glu Asn Lys Asn Gly Asn Pro
 50                  55                  60

His Arg Glu Asn Leu Arg Ile Ser Lys Ser Ser Phe Gln Val Thr Thr
 65                  70                  75                  80

Cys Lys Leu His Gly Gly Ser Pro Trp Pro Pro Cys Gln Tyr Arg Ala
                85                  90                  95

Thr Ala Gly Phe Arg Asn Val Val Val Ala Cys Glu Asn Gly Leu Pro
            100                 105                 110

Val His Leu Asp Gln Ser Ile Phe Arg Arg Pro Gly Gly Gly Gly Ser
        115                 120                 125

```
Asn Ser Asp Ser Glu Cys Pro Leu Ser His Asp Gly Tyr Cys Leu His
        130                 135                 140
Asp Gly Val Cys Met Tyr Ile Glu Ala Leu Asp Lys Tyr Ala Cys Asn
145                 150                 155                 160
Cys Val Val Gly Tyr Ile Gly Glu Arg Cys Gln Tyr Arg Asp Leu Lys
                165                 170                 175
Trp Trp Glu Leu Arg
            180

<210> SEQ ID NO 19
<211> LENGTH: 176
<212> TYPE: PRT
<213> ORGANISM: Artificial Sequence
<220> FEATURE:
<223> OTHER INFORMATION: amino acid sequnce of fusion protein

<400> SEQUENCE: 19

Asn Ser Asp Ser Glu Cys Pro Leu Ser His Asp Gly Tyr Cys Leu His
 1               5                  10                  15
Asp Gly Val Cys Met Tyr Ile Glu Ala Leu Asp Lys Tyr Ala Cys Asn
            20                  25                  30
Cys Val Val Gly Tyr Ile Gly Glu Arg Cys Gln Tyr Arg Asp Leu Lys
        35                  40                  45
Trp Trp Glu Leu Arg Gln Asp Asn Ser Arg Tyr Thr His Phe Leu Thr
    50                  55                  60
Gln His Tyr Asp Ala Lys Pro Gln Gly Arg Asp Asp Arg Tyr Cys Glu
65                  70                  75                  80
Ser Ile Met Arg Arg Arg Gly Leu Thr Ser Pro Cys Lys Asp Ile Asn
                85                  90                  95
Thr Phe Ile His Gly Asn Lys Arg Ser Ile Lys Ala Ile Cys Glu Asn
            100                 105                 110
Lys Asn Gly Asn Pro His Arg Glu Asn Leu Arg Ile Ser Lys Ser Ser
        115                 120                 125
Phe Gln Val Thr Thr Cys Lys Leu His Gly Gly Ser Pro Trp Pro Pro
    130                 135                 140
Cys Gln Tyr Arg Ala Thr Ala Gly Phe Arg Asn Val Val Val Ala Cys
145                 150                 155                 160
Glu Asn Gly Leu Pro Val His Leu Asp Gln Ser Ile Phe Arg Arg Pro
                165                 170                 175

<210> SEQ ID NO 20
<211> LENGTH: 177
<212> TYPE: PRT
<213> ORGANISM: Artificial Sequence
<220> FEATURE:
<223> OTHER INFORMATION: amino acid sequence of fusion protein

<400> SEQUENCE: 20

Asn Ser Asp Ser Glu Cys Pro Leu Ser His Asp Gly Tyr Cys Leu His
 1               5                  10                  15
Asp Gly Val Cys Met Tyr Ile Glu Ala Leu Asp Lys Tyr Ala Cys Asn
            20                  25                  30
Cys Val Val Gly Tyr Ile Gly Glu Arg Cys Gln Tyr Arg Asp Leu Lys
        35                  40                  45
Trp Trp Glu Leu Arg Gly Gln Asp Asn Ser Arg Tyr Thr His Phe Leu
    50                  55                  60
Thr Gln His Tyr Asp Ala Lys Pro Gln Gly Arg Asp Asp Arg Tyr Cys
65                  70                  75                  80
```

```
Glu Ser Ile Met Arg Arg Gly Leu Thr Ser Pro Cys Lys Asp Ile
                85                  90                  95

Asn Thr Phe Ile His Gly Asn Lys Arg Ser Ile Lys Ala Ile Cys Glu
            100                 105                 110

Asn Lys Asn Gly Asn Pro His Arg Glu Asn Leu Arg Ile Ser Lys Ser
        115                 120                 125

Ser Phe Gln Val Thr Thr Cys Lys Leu His Gly Gly Ser Pro Trp Pro
    130                 135                 140

Pro Cys Gln Tyr Arg Ala Thr Ala Gly Phe Arg Asn Val Val Val Ala
145                 150                 155                 160

Cys Glu Asn Gly Leu Pro Val His Leu Asp Gln Ser Ile Phe Arg Arg
                165                 170                 175

Pro
```

```
<210> SEQ ID NO 21
<211> LENGTH: 181
<212> TYPE: PRT
<213> ORGANISM: Artificial Sequence
<220> FEATURE:
<223> OTHER INFORMATION: amino acid sequence of fusion protein

<400> SEQUENCE: 21

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg Gly Gly Gly Ser Gln Asp Asn Ser Arg Tyr
    50                  55                  60

Thr His Phe Leu Thr Gln His Tyr Asp Ala Lys Pro Gln Gly Arg Asp
65                  70                  75                  80

Asp Arg Tyr Cys Glu Ser Ile Met Arg Arg Gly Leu Thr Ser Pro
                85                  90                  95

Cys Lys Asp Ile Asn Thr Phe Ile His Gly Asn Lys Arg Ser Ile Lys
            100                 105                 110

Ala Ile Cys Glu Asn Lys Asn Gly Asn Pro His Arg Glu Asn Leu Arg
        115                 120                 125

Ile Ser Lys Ser Ser Phe Gln Val Thr Thr Cys Lys Leu His Gly Gly
    130                 135                 140

Ser Pro Trp Pro Pro Cys Gln Val Thr Thr Cys Ala Gly Phe Arg Asn
145                 150                 155                 160

Val Val Val Ala Cys Glu Asn Gly Leu Pro Val His Leu Asp Gln Ser
                165                 170                 175

Ile Phe Arg Arg Pro
            180
```

```
<210> SEQ ID NO 22
<211> LENGTH: 186
<212> TYPE: PRT
<213> ORGANISM: Artificial Sequence
<220> FEATURE:
<223> OTHER INFORMATION: amino acid sequence of fusion protein

<400> SEQUENCE: 22

Asn Ser Asp Ser Glu Cys Pro Leu Ser His Asp Gly Tyr Cys Leu His
1               5                   10                  15
```

```
Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg Gly Gly Gly Ser Gly Gly Gly Gly Ser Gln
50                  55                  60

Asp Asn Ser Arg Tyr Thr His Phe Leu Thr Gln His Tyr Asp Ala Lys
65                  70                  75                  80

Pro Gln Gly Arg Asp Asp Arg Tyr Cys Glu Ser Ile Met Arg Arg Arg
                85                  90                  95

Gly Leu Thr Ser Pro Cys Lys Asp Ile Asn Thr Phe Ile His Gly Asn
            100                 105                 110

Lys Arg Ser Ile Lys Ala Ile Cys Glu Asn Lys Asn Gly Asn Pro His
        115                 120                 125

Arg Glu Asn Leu Arg Ile Ser Lys Ser Ser Phe Gln Val Thr Thr Cys
    130                 135                 140

Lys Leu His Gly Gly Ser Pro Trp Pro Pro Cys Gln Val Thr Thr Cys
145                 150                 155                 160

Ala Gly Phe Arg Asn Val Val Val Ala Cys Glu Asn Gly Leu Pro Val
                165                 170                 175

His Leu Asp Gln Ser Ile Phe Arg Arg Pro
            180                 185

<210> SEQ ID NO 23
<211> LENGTH: 543
<212> TYPE: DNA
<213> ORGANISM: Artificial Sequence
<220> FEATURE:
<223> OTHER INFORMATION: fusion gene of angiogenin and hEGF

<400> SEQUENCE: 23
aatagtgact ccgaatgccc gctgagccat gacggctact gcctgcacga cggcgtatgc        60
atgtacatcg aagcactgga caaatacgcg tgcaactgtg ttgttggcta catcggcgag       120
cgctgtcagt accgtgacct taagtggtgg gaactgcgcg gaggaggagg atcccaggat       180
aactccaggt acacacactt cctgacccag cactatgatg ccaaaccaca gggccgggat       240
gacagatact gtgaaagcat catgaggaga cggggcctga cctcaccctg caagacatc       300 aacacattta ttcatggcaa caagcgcagc atcaaggcca tctgtgaaaa caagaatgga       360
aaccctcaca gagaaaacct aagaataagc aagtcttctt tccaggtcac cacttgcaag       420
ctacatggag ttccccctg gcctccatgc cagtaccgag ccacagcggg gttcagaaac       480
gttgttgttg cttgtgaaaa tggcttacct gtccacttgg atcagtcaat tttccgtcgc       540
ccg                                                                    543

<210> SEQ ID NO 24
<211> LENGTH: 558
<212> TYPE: DNA
<213> ORGANISM: Artificial Sequence
<220> FEATURE:
<223> OTHER INFORMATION: fusion gene of angiogenin and hEGF

<400> SEQUENCE: 24
aatagtgact ccgaatgccc gctgagccat gacggctact gcctgcacga cggcgtatgc        60
atgtacatcg aagcactgga caaatacgcg tgcaactgtg ttgttggcta catcggcgag       120
cgctgtcagt accgtgacct taagtggtgg gaactgcgcg gaggaggagg atccggagga       180
```

```
ggaggatcac aggataactc caggtacaca cacttcctga cccagcacta tgatgccaaa      240
ccacagggcc gggatgacag atactgtgaa agcatcatga ggagacgggg cctgacctca      300
ccctgcaaag acatcaacac atttattcat ggcaacaagc gcagcatcaa ggccatctgt      360
gaaaacaaga atggaaaccc tcacagagaa aacctaagaa taagcaagtc ttctttccag      420
gtcaccactt gcaagctaca tggaggttcc cctggcctc catgccagta ccgagccaca       480
gcggggttca gaaacgttgt tgttgcttgt gaaaatggct tacctgtcca cttggatcag      540
tcaattttcc gtcgcccg                                                    558

<210> SEQ ID NO 25
<211> LENGTH: 30
<212> TYPE: DNA
<213> ORGANISM: Artificial Sequence
<220> FEATURE:
<223> OTHER INFORMATION: primer containing NdeI restriction site

<400> SEQUENCE: 25
gcgcatatga atagtgactc cgaatgtccg                                       30

<210> SEQ ID NO 26
<211> LENGTH: 28
<212> TYPE: DNA
<213> ORGANISM: Artificial Sequence
<220> FEATURE:
<223> OTHER INFORMATION: primer containing BamHI restriction site

<400> SEQUENCE: 26
aggatcctcc tcctccgcgc agttccca                                         28

<210> SEQ ID NO 27
<211> LENGTH: 30
<212> TYPE: DNA
<213> ORGANISM: Artificial Sequence
<220> FEATURE:
<223> OTHER INFORMATION: primer containing BamHI restriction site

<400> SEQUENCE: 27
cggatcccag gataactcca ggtacacaca                                       30

<210> SEQ ID NO 28
<211> LENGTH: 35
<212> TYPE: DNA
<213> ORGANISM: Artificial Sequence
<220> FEATURE:
<223> OTHER INFORMATION: primer for 415bp DNA fragment

<400> SEQUENCE: 28
aggatccgga ggaggaggat cacaggataa ctcca                                 35

<210> SEQ ID NO 29
<211> LENGTH: 927
<212> TYPE: DNA
<213> ORGANISM: Artificial Sequence
<220> FEATURE:
<223> OTHER INFORMATION: fusion gene of angiogenin and hEGF

<400> SEQUENCE: 29
caggataact ccaggtacac acacttcctg acccagcact atgatgccaa accacagggc      60
cgggatgaca gatactgtga agcatcatg aggagacggg gcctgacctc accctgcaaa      120
gacatcaaca catttattca tggcaacaag cgcagcatca aggccatctg tgaaaacaag      180
```

-continued

| | |
|---|---|
| aatggaaacc ctcacagaga aaacctaaga ataagcaagt cttctttcca ggtcaccact | 240 |
| tgcaagctac atggaggttc ccctggcct ccatgccagt accgagccac agcggggttc | 300 |
| agaaacgttg ttgttgcttg tgaaaatggc ttacctgtcc acttggatca gtcaatttc | 360 |
| cgtcgcccgg gaggaggagg atccaatagt gactccgaat gcccgctgag ccatgacggc | 420 |
| tactgcctgc acgacggcgt atgcatgtac atcgaagcac tggacaaata cgcgtgcaac | 480 |
| tgtgttgttg gctacatcgg cgagcgctgt cagtaccgtg accttaagtg gtgggaactg | 540 |
| cgcggaggag gaggatccca ggataactcc aggtacacac acttcctgac ccagcactat | 600 |
| gatgccaaac cacagggccg ggatgacaga tactgtgaaa gcatcatgag gagacggggc | 660 |
| ctgacctcac cctgcaaaga catcaacaca tttattcatg caacaagcg cagcatcaag | 720 |
| gccatctgtg aaaacaagaa tggaaaccct cacagagaaa acctaagaat aagcaagtct | 780 |
| tctttccagg tcaccacttg caagctatat ggaggttccc cctggcctcc atgccagtac | 840 |
| cgagccacag cggggttcag aaacgttgtt gttgcttgtg aaaatggctt acctgtccac | 900 |
| ttggatcagt caattttccg tcgcccg | 927 |

<210> SEQ ID NO 30
<211> LENGTH: 717
<212> TYPE: DNA
<213> ORGANISM: Artificial Sequence
<220> FEATURE:
<223> OTHER INFORMATION: fusion gene of angiogenin and hEGF

<400> SEQUENCE: 30

| | |
|---|---|
| aatagtgact ccgaatgccc gctgagccat gacggctact gcctgcacga cggcgtatgc | 60 |
| atgtacatcg aagcactgga caaatacgcg tgcaactgtg ttgttggcta catcggcgag | 120 |
| cgctgtcagt accgtgacct taagtggtgg gaactgcgcg aggaggagg atcccaggat | 180 |
| aactccaggt acacacactt cctgacccag cactatgatg ccaaaccaca gggccgggat | 240 |
| gacagatact gtgaaagcat catgaggaga cggggcctga cctcaccctg caaagacatc | 300 |
| aacacattta ttcatggcaa caagcgcagc atcaaggcca tctgtgaaaa caagaatgga | 360 |
| aaccctcaca gagaaaacct aagaataagc aagtcttctt tccaggtcac cacttgcaag | 420 |
| ctacatggag gttccccctg gcctccatgc cagtaccgag ccacagcggg gttcagaaac | 480 |
| gttgttgttg cttgtgaaaa tggcttacct gtccacttgg atcagtcaat tttccgtcgc | 540 |
| ccggaggag gaggatccaa tagtgactcc gaatgcccgc tgagccatga cggctactgc | 600 |
| ctgcacgacg gcgtatgcat gtacatcgaa gcactggaca aatacgcgtg caactgtgtt | 660 |
| gttggctaca tcggcgagcg ctgtcagtac cgtgacctta agtggtggga actgcgc | 717 |

<210> SEQ ID NO 31
<211> LENGTH: 309
<212> TYPE: PRT
<213> ORGANISM: Artificial Sequence
<220> FEATURE:
<223> OTHER INFORMATION: amino acid sequence of fusion protein

<400> SEQUENCE: 31

Gln Asp Asn Ser Arg Tyr Thr His Phe Leu Thr Gln His Tyr Asp Ala
 1               5                  10                  15

Lys Pro Gln Gly Arg Asp Asp Arg Tyr Cys Glu Ser Ile Met Arg Arg
            20                  25                  30

Arg Gly Leu Thr Ser Pro Cys Lys Asp Ile Asn Thr Phe Ile His Gly
        35                  40                  45

```
Asn Lys Arg Ser Ile Lys Ala Ile Cys Glu Asn Lys Asn Gly Asn Pro
     50                  55                  60

His Arg Glu Asn Leu Arg Ile Ser Lys Ser Ser Phe Gln Val Thr Thr
 65                  70                  75                  80

Cys Lys Leu His Gly Gly Ser Pro Trp Pro Cys Gln Val Thr Thr
                 85                  90                  95

Cys Ala Gly Phe Arg Asn Val Val Ala Cys Glu Asn Gly Leu Pro
                100                 105                 110

Val His Leu Asp Gln Ser Ile Phe Arg Arg Pro Gly Gly Gly Ser
             115                 120                 125

Asn Ser Asp Ser Glu Cys Pro Leu Ser His Asp Gly Tyr Cys Leu His
    130                 135                 140

Asp Gly Val Cys Met Tyr Ile Glu Ala Leu Asp Lys Tyr Ala Cys Asn
145                 150                 155                 160

Cys Val Val Gly Tyr Ile Gly Glu Arg Cys Gln Tyr Arg Asp Leu Lys
                165                 170                 175

Trp Trp Glu Leu Arg Gly Gly Gly Ser Gln Asp Asn Ser Arg Tyr
             180                 185                 190

Thr His Phe Leu Thr Gln His Tyr Asp Ala Lys Pro Gln Gly Arg Asp
        195                 200                 205

Asp Arg Tyr Cys Glu Ser Ile Met Arg Arg Gly Leu Thr Ser Pro
        210                 215                 220

Cys Lys Asp Ile Asn Thr Phe Ile His Gly Asn Lys Arg Ser Ile Lys
225                 230                 235                 240

Ala Ile Cys Glu Asn Lys Asn Gly Asn Pro His Arg Glu Asn Leu Arg
                245                 250                 255

Ile Ser Lys Ser Ser Phe Gln Val Thr Thr Cys Lys Leu His Gly Gly
            260                 265                 270

Ser Pro Trp Pro Cys Gln Val Thr Thr Cys Ala Gly Phe Arg Asn
            275                 280                 285

Val Val Val Ala Cys Glu Asn Gly Leu Pro Val His Leu Asp Gln Ser
    290                 295                 300

Ile Phe Arg Arg Pro
305

<210> SEQ ID NO 32
<211> LENGTH: 239
<212> TYPE: PRT
<213> ORGANISM: Artificial Sequence
<220> FEATURE:
<223> OTHER INFORMATION: amino acid sequence of fusion protein

<400> SEQUENCE: 32

Asn Ser Asp Ser Glu Cys Pro Leu Ser His Asp Gly Tyr Cys Leu His
  1               5                  10                  15

Asp Gly Val Cys Met Tyr Ile Glu Ala Leu Asp Lys Tyr Ala Cys Asn
             20                  25                  30

Cys Val Val Gly Tyr Ile Gly Glu Arg Cys Gln Tyr Arg Asp Leu Lys
         35                  40                  45

Trp Trp Glu Leu Arg Gly Gly Gly Ser Gln Asp Asn Ser Arg Tyr
     50                  55                  60

Thr His Phe Leu Thr Gln His Tyr Asp Ala Lys Pro Gln Gly Arg Asp
 65                  70                  75                  80

Asp Arg Tyr Cys Glu Ser Ile Met Arg Arg Gly Leu Thr Ser Pro
                 85                  90                  95
```

-continued

```
Cys Lys Asp Ile Asn Thr Phe Ile His Gly Asn Lys Arg Ser Ile Lys
            100                 105                 110

Ala Ile Cys Glu Asn Lys Asn Gly Asn Pro His Arg Glu Asn Leu Arg
            115                 120             125

Ile Ser Lys Ser Ser Phe Gln Val Thr Thr Cys Lys Leu His Gly Gly
            130             135             140

Ser Pro Trp Pro Pro Cys Gln Val Thr Thr Cys Ala Gly Phe Arg Asn
145                 150                 155                 160

Val Val Val Ala Cys Glu Asn Gly Leu Pro Val His Leu Asp Gln Ser
                165                 170             175

Ile Phe Arg Arg Pro Gly Gly Gly Gly Ser Asn Ser Asp Ser Glu Cys
            180             185                 190

Pro Leu Ser His Asp Gly Tyr Cys Leu His Asp Gly Val Cys Met Tyr
            195             200                 205

Ile Glu Ala Leu Asp Lys Tyr Ala Cys Asn Cys Val Val Gly Tyr Ile
            210             215             220

Gly Glu Arg Cys Gln Tyr Arg Asp Leu Lys Trp Trp Glu Leu Arg
225                 230             235
```